US007094766B1

(12) United States Patent
Gilchrest et al.

(10) Patent No.: US 7,094,766 B1
(45) Date of Patent: *Aug. 22, 2006

(54) USE OF LOCALLY APPLIED DNA FRAGMENTS

(75) Inventors: Barbara A. Gilchrest, Boston, MA (US); Mina Yaar, Sharon, MA (US); Mark Eller, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/540,843

(22) Filed: Mar. 31, 2000

Related U.S. Application Data

(63) Continuation-in-part of application No. 09/048,927, filed on Mar. 26, 1998, now Pat. No. 6,147,056, which is a continuation-in-part of application No. 08/952,697, filed on Nov. 30, 1998, now abandoned, and a continuation-in-part of application No. PCT/US96/08386, filed on Jun. 3, 1996, which is a continuation-in-part of application No. 08/467,012, filed on Jun. 6, 1995, now Pat. No. 5,955,059.

(51) Int. Cl.
*A61K 31/70* (2006.01)
*A01N 43/04* (2006.01)

(52) U.S. Cl. ...................................................... 514/44
(58) Field of Classification Search ................ 514/44, 514/48; 424/59, 450; 435/455, 320.1, 720.1
See application file for complete search history.

(56) References Cited

U.S. PATENT DOCUMENTS

| | | | | |
|---|---|---|---|---|
| 3,937,809 | A | | 2/1976 | Jacobi ........................ 424/60 |
| 4,419,343 | A | | 12/1983 | Pauly .......................... 424/59 |
| 4,508,703 | A | | 4/1985 | Redziniak et al. ............ 424/38 |
| 4,621,023 | A | | 11/1986 | Redziniak et al. ....... 428/402.2 |
| 5,077,211 | A | | 12/1991 | Yarosh ....................... 435/193 |
| 5,455,029 | A | * | 10/1995 | Hartman et al. ........... 424/94.4 |
| 5,470,577 | A | | 11/1995 | Gilchrest et al. ........... 424/450 |
| 5,532,001 | A | | 7/1996 | Gilchrest et al. ........... 424/450 |
| 5,580,547 | A | | 12/1996 | Gilchrest et al. ............. 424/59 |
| 5,583,016 | A | * | 12/1996 | Villeponteau et al. ..... 435/91.3 |
| 5,585,479 | A | * | 12/1996 | Hoke et al. ................ 536/24.5 |
| 5,599,672 | A | | 2/1997 | Liang et al. ................... 435/6 |
| 5,643,556 | A | | 7/1997 | Gilchrest et al. ............. 424/59 |
| 5,643,890 | A | | 7/1997 | Iversen et al. ................ 514/44 |
| 5,686,306 | A | * | 11/1997 | West et al. ................. 435/346 |
| 5,858,987 | A | * | 1/1999 | Beer-Romero et al. ....... 574/44 |
| 5,879,713 | A | | 3/1999 | Roth et al. ................... 424/489 |
| 5,955,059 | A | * | 9/1999 | Gilchrest et al. ............. 424/59 |
| 6,007,989 | A | | 12/1999 | West et al. ...................... 435/6 |
| 6,015,710 | A | * | 1/2000 | Shay et al. ................... 435/375 |
| 6,020,138 | A | * | 2/2000 | Akhavan-Tafti ................ 435/6 |
| 6,046,307 | A | * | 4/2000 | Shay et al. ................... 530/324 |
| 6,103,243 | A | * | 8/2000 | Russell-Jones et al. 424/195.11 |
| 6,147,056 | A | * | 11/2000 | Gilchrest et al. .............. 514/44 |
| 6,194,206 | B1 | * | 2/2001 | West et al. ................... 435/375 |

FOREIGN PATENT DOCUMENTS

| | | |
|---|---|---|
| EP | 0 035 384 A2 | 9/1981 |
| GB | 2 336 157 A | 10/1999 |
| WO | WO 93/09788 | 5/1993 |
| WO | WO 93/22431 | 11/1993 |
| WO | WO 95/01773 | 1/1995 |
| WO | WO 95/07362 | 3/1995 |
| WO | WO 95/09175 | 4/1995 |
| WO | WO 97/08314 | 8/1996 |
| WO | WO 96/40989 | 12/1996 |
| WO | WO 97/44450 | 11/1997 |
| WO | WO 98/36066 | 2/1998 |
| WO | WO 99/03507 | 1/1999 |

OTHER PUBLICATIONS

F Plenat, Molecular Medicine Today, "Animal models of antisense oligonucleotides: lessons for use in humans," Jun. 1996, pp. 250-257.*

PTC Ho et al., Seminars in Oncology, "Antisense Oligonucleotides as Therapeutics for Malignant Diseases," Apr. 1997, vol. 24, No. 2, pp. 187-202.*

RA Stull et al., Pharmaceutical Research, "Antigene, Ribozyme and Aptamer Nucleic Acid Drugs:Progress and Prospects," 1995, vol. 12, No. 4, pp. 465-483.*

AD Branch, TIBS, "A good antisense molecule is hard to find," 1998, vol. 23, pp. 45-50.*

IM Verma et al., Nature, "Gene therapy-promises, problems and prospects," Sep. 1997, vol. 389, pp. 239-242.*

WF Anderson, Nature, "Human gene therapy," Apr. 1998, vol. 392, pp. 25-30.*

D Voet et al., Biochemistry, "DNA Replication, Repair and Recombination," 1990, Chap.31, pp. 967-972.*

DT Page et al., DDT, "Innovations in oral gene delivery:challenges and potentials," Jan. 2001, vol. 6, No. 2, pp. 92-101.*

(Continued)

*Primary Examiner*—Brian Whiteman
(74) *Attorney, Agent, or Firm*—Howrey LLP; David W. Clough

(57) ABSTRACT

Methods of treatment or prevention of hyperproliferative diseases or pre-cancerous conditions affecting epithelial cells, such as psoriasis, vitiligo, atopic dermatitis, or hyperproliferative or UV-responsive dermatoses, hyperproliferative or allergically mediated diseases of other epithelia and methods for reducing photoaging, or oxidative stress or for prophylaxis against or reduction in the likelihood of the development of skin cancer, are disclosed.

57 Claims, 18 Drawing Sheets

OTHER PUBLICATIONS

T Ohnuma et al.,Anticancer Research, "Inhibitory Effects of Telomere-Mimic Phosphorothioate Oligonucleotides on Various Human Tumor Cells in Vitro," 1997, 17, pp. 2455-2458.*

TJ Page et al.,Experimental Cell Research, "The Cytotoxic Effects of Single-Stranded Telomere Mimics on OMA-BL1 Cells," 1999, 252, pp. 41-49.*

Gomez-Navarro et al. Gene Therapy for Cancer, European Journal of Cancer, vol. 35, pp. 867-885, 1999.*

Niggli, H.J., et al., "Sunlight-Induced Pyrimidine Dimers In Human Skin Fibroblasts In Comparison With Dimerization After Artificial UV-Irradiation," *Photochemistry and Photobiology*, 48(3):353-356 (1988).

Jayaraman, L., et al., "Activation of p53 Sequence-Specific DNA Binding by Short Single Strands of DNA Requires the p53 C-Terminus," *Cell*, 81:1021-1029 (1995).

Kern S.E., et al., "Oncogenic Forms of p53 Inhibit p53-Regulated Gene Expression," *Science*, 256:827-830 (1992).

Walworth, N.C., et al., "rad-Dependent Response of the chkl-Encoded Protein Kinase at the DNA Damage Checkpoint," *Science*, 271:353-356 (1996).

El-Deiry, W.S., et al., "WAF1, a Potential Mediator of p53 Tumor Suppression," *Cell*, 75:817-825 (1993).

Lu, X., et al., "Differential Induction of Transcriptionally Active p53 Following UV or Ionizing Radiation: Defects in Chromosome Instability Syndromes?" *Cell*, 75:765-778 (1993).

Kastan, M.B., et al., "A Mammalian Cell Cycle Checkpoint Pathway Utilizing p53 and GADD45 Is Defective in Ataxia-Telangiectasia," *Cell*, 71:587-597 (1992).

Hupp, T.R., et al., "Small Peptides Activate the Latent Sequence-Specific DNA Binding Function of p53," *Cell*, 83:237-245 (1995).

Sanchez, Y., et al., "Regulation of RAD53 by the ATM-Like Kinases MEC1 and TEL1 in Yeast Cell Cycle Checkpoint Pathways," *Science*, 271:357-360 (1996).

Fritsche, M., et al., "Induction of nuclear accumulation of the tumor-suppressor protein p53 by DNA-damaging agents," *Oncogene* 8:307-318 (1993).

Mitsudomi, T., et al., "p53 gene mutations in non-small-cell lung cancer cell lines and their correlation with the presence of ras mutations and clinical features," *Oncogene* 7:171-180 (1992).

Nelson, W.G., et al., "DNA Strand Breaks: the DNA Template Alterations That Trigger p53-Dependent DNA Damage Response Pathways," *Mol. and Cell. Biol.* 14(3):1815-1823 (1994).

Wei, Q., et al., "DNA repair and aging in basal cell carcinoma: A molecular epidemiology study," *Proc. Natl. Acad. Sci. USA* 90:1614-1618 (1993).

Yaar, M., et al., "The trk Family of Receptors Mediates Nerve Growth Factor and Neurotrophin-3 Effects in Melanocytes," *J. Clin. Invest* 94:1550-1562 (1994).

Mitchell, D.L. and Karentz, D., "The Induction and Repair of DNA Photodamage in the Environment," In *Environment UV Photobiology*, A.R. Young, et al., eds. (NY: Plenum Press), pp. 345-377 (1993).

Pedeux, R., et al., "Thymidine Dinucleotides Induce S Phase Cell Cycle Arrest in Addition to Increased Melanogenesis in Human Melanocytes," *Journal of Investigative Dermatology*, 111:472-477 (1998).

Harley, C.B., et al., "Telomerase, Checkpoints and Cancer," In *Cancer Surveys—Advances and Prospects in Clinical, Epidemiological and Laboratory Oncology*, Cold Spring Harbor Laboratory Press, 29:263-284 (1997).

Yaar, M., et al., "Aging Versus Photoaging: Postulated Mechanisms and Effectors," *The Society for Investigative Dermatology Symposium Proceedings*, 3:47-51 (1998).

Parris, C.N., et al., "Telomerase activity in melanoma and non-melanoma skin cancer," *British Jour. of Cancer*, 79(1):47-53 (1999).

Wu, K., et al., "Telomerase Activity and Telomere Length in Lymphocytes from Patients with Cutaneous T-Cell Lymphoma," *Cancer*, 86(6):1056-1063 (1999).

Akiyama, M., et al, "Cytostatic Concentrations of Anticancer Agents do not Affect Telomerase Activity of Leukaemic Cells *In Vitro,*" *European Jour. of Cancer*, 35(2):309-315 (1999).

Balasubramanian, S., et al., "Activation of telomerase and its association with G1-phase of the cell cycle during UVB-induced skin tumorigenesis in SKH-1 hairless mouse," *Oncogene*, 18:1297-1302 (1999).

Wright, W.E. et al., "Experimental elongation of telomeres extends the lifespan of immortal x normal cell hybrids," *The EMBO Journal*, 15(7):1734-1741 (1996).

Mata, J. et al. "A Hexameric Phosporothioate Oligonucleotide Telomerase Inhibitor Arrests Growth of Burkitts's Lymphoma Cells *in Vitro* and *in Vivo,*" *Toxicol. Appl. Pharmacol.* 144:189-197 (1997).

Eller, M.S. et al., "The Effect of Oligonucleotide Size and 5001' Phosphate on Stimulation of Melanogenesis," *J. Invest. Dermatol.* Abstract No. 113; vol. 112, No. 4, p. 541 (1999).

* cited by examiner

SEQUENCE LISTING

<160> NUMBER OF SEQ ID NOS: 12

<210> SEQ ID NO 1
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 1 gagtatgag                                                                  9

<210> SEQ ID NO 2
<211> LENGTH: 9
<212> TYPE: DNA
<213> ORGANISM: Artificial Sequence
<220> FEATURE:
<223> OTHER INFORMATION: Synthetic DNA Fragment

<400> SEQUENCE: 2 taggaggat                                                                  9

<210> SEQ ID NO 3
<211> LENGTH: 7
<212> TYPE: DNA
<213> ORGANISM: Artificial Sequence
<220> FEATURE:
<223> OTHER INFORMATION: Synthetic DNA Fragment

<400> SEQUENCE: 3 agtatga                                                                    7

<210> SEQ ID NO 4
<211> LENGTH: 5
<212> TYPE: DNA
<213> ORGANISM: Artificial Sequence
<220> FEATURE:
<223> OTHER INFORMATION: Synthetic DNA Fragment

<400> SEQUENCE: 4 gtatg                                                                      5

<210> SEQ ID NO 5
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 5
gttagggtta g                                                              11

<210> SEQ ID NO 6
<211> LENGTH: 5
<212> TYPE: DNA
<213> ORGANISM: Artificial Sequence
<220> FEATURE:
<223> OTHER INFORMATION: Synthetic DNA Fragment

<400> SEQUENCE: 6 catac                                                                      5

<210> SEQ ID NO 7
<211> LENGTH: 7

```
<212> TYPE: DNA
<213> ORGANISM: Artificial Sequence
<220> FEATURE:
<223> OTHER INFORMATION: Synthetic DNA Fragment

<400> SEQUENCE: 7 agtatga                                                                  7

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA Fragment

<400> SEQUENCE: 8
gcatgcatgc attacgtacg                                                   20

<210> SEQ ID NO 9
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 9
ctaaccctaa c                                                            11

<210> SEQ ID NO 10
<211> LENGTH: 11
<212> TYPE: DNA
<213> ORGANISM: Artificial Sequence
<220> FEATURE:
<223> OTHER INFORMATION: Synthetic DNA Fragment

<400> SEQUENCE: 10
gatcgatcga t                                                            11

<210> SEQ ID NO 11
<211> LENGTH: 6
<212> TYPE: DNA
<213> ORGANISM: Artificial Sequence
<220> FEATURE:
<223> OTHER INFORMATION: Synthetic DNA Fragment

<400> SEQUENCE: 11 ttaggg                                                                   6

<210> SEQ ID NO 12
<211> LENGTH: 6
<212> TYPE: DNA
<213> ORGANISM: Artificial Sequence
<220> FEATURE:
<223> OTHER INFORMATION: Synthetic DNA Fragment

<400> SEQUENCE: 12 ccctaa                                                                   6
```

USE OF LOCALLY APPLIED DNA FRAGMENTS

RELATED APPLICATIONS

This application is a Continuation-in-Part of application Ser. No. 09/048,927 filed Mar. 26, 1998, now U.S. Pat. No. 6,147,056, which is a Continuation-in-Part of U.S. National Phase of PCT/US96/08386 filed Jun. 3, 1996 and assigned U.S. application Ser. No. 08/952,697, filed Nov. 30, 1998, now abandoned, which is a Continuation-in-Part of application Ser. No. 08/467,012 filed Jun. 6, 1995, now U.S. Pat. No. 5,955,059 the entire teachings of which are incorporated herein by reference.

BACKGROUND OF THE INVENTION

Human skin consists of two layers, the dermis and the epidermis. The epidermis, which is the uppermost of the two skin layers, encompasses many different cell types, including melanocytes and keratinocytes. Melanocytes are specialized cells in the basal layer of the epidermis which synthesize melanin; the melanin is then packaged into melanosomes and then transported into keratinocytes. Exposure of skin to the sun results in vitamin D synthesis, sunburn (erythema), and tanning, the skin's major form of endogenous protection against subsequent skin damage from ultraviolet (UV) irradiation. Various morphologic and enzymatic changes occur at the cellular level in epidermal melanocytes in response to UV irradiation. Melanin, which is increased in "tanned" skin, serves as a filter with absorbance within the UV range and provides photoprotection for the individual.

The peak action spectrum for erythema is in the UV-B range, 290–305 nm. UV-B rays are absorbed by proteins and nucleic acids of the epidermis, causing the production of many photo products including thymine dimers, which are known to be formed by UV irradiation of nuclear DNA and to be excised from the DNA strand by the action of highly specific enzymes, including endonucleases. If not removed, these dimers can stall DNA replication forks generating regions of single-stranded DNA. Failure to remove thymine dimers and other forms of DNA damage in the genome may lead to somatic mutations resulting in carcinogenesis.

In bacteria it is known that single-stranded DNA released as fragments during the course of DNA repair or exposed at stalled replication forks can interact with nuclear proteins which then regulate the expression of specific genes in the DNA as part of the organism's SOS response to UV damage. The tanning response of skin might reasonably be considered part of the analogous SOS response in mammalian skin. The precise stimulus for UV-induced tanning, however, remains unknown.

UV irradiation is successfully used in phototherapy and photochemotherapy for certain dermatological conditions. For example, psoriasis is a common dermatologic disease affecting 1 to 2 percent of the population. Psoriasis can be treated with UV-B irradiation, either alone or in conjunction with agents such as coal tar or anthralin, or with UV-A irradiation in combination with psoralens (PUVA therapy). Other diseases which respond to UV irradiation treatment include atopic dermatitis and vitiligo. Despite the benefits of phototherapy and photochemotherapy, these treatments carry the same risks as chronic exposure to sun, including wrinkling, "photoaging," and skin cancer.

SUMMARY OF THE INVENTION

The present invention is drawn to compounds that induce UV-mimetic activity in vitro and in vivo and methods of using such UV-mimetics. As described herein, UV-mimetic activity includes induction of DNA repair mechanisms, inhibition of proliferation, induction of apoptosis and increased melanin production (tanning). The compounds and methods of the present invention include oligonucleotides, polynucleotides, DNA fragments, nucleotides, dinucleotides and dinucleotide dimers. The compounds of the present invention can be modified, for example, oligonucleotides having modified back bone structure. The oligonucleotide can contain a 5' phosphate.

One embodiment of the present invention comprises a method of increasing melanin production in epidermal cells, comprising contacting said cells with a mimic of telomere disruption, wherein said inhibitor comprises at least one oligonucleotide. Increased melanin production results in tanning of mammalian skin.

Another embodiment comprises increasing melanin production in epidermal cells, comprising contacting the cells with an effective amount of at least one oligonucleotide, wherein said oligonucleotide comprises at least one sequence selected from the group consisting of SEQ ID NOs: 5, 7 and 8 or portion thereof and their complementary sequences. Another embodiment comprises increasing DNA repair in epithelial cells, comprising contacting said cells with an effective amount of oligonucleotide, wherein said oligonucleotide comprises a sequence selected from the group consisting of SEQ ID NOs: 5, 7 and 8, or a portion thereof. Another embodiment comprises inhibiting proliferation of epithelial cells, comprising contacting said cells with an effective amount of a oligonucleotide, wherein said oligonucleotide comprises a sequence selected from the group consisting of SEQ ID NOs: 5, 7 and 8, or a portion thereof. Another embodiment comprises promoting immunosuppression in epithelial tissue and cells, comprising contacting said epithelium and cells with an effective amount of at least one oligonucleotide, wherein said oligonucleotide comprises a sequence selected from the group consisting of SEQ ID NOs: 5, 7 and 8 or portion thereof. Another embodiment comprises promoting apoptosis of epithelial cells, wherein said cells contain damaged or undamaged genomic DNA, comprising contacting said cells with an effective amount of at least one oligonucleotide, wherein said oligonucleotide comprises a sequence selected from the group consisting of SEQ ID NOs: 5, 7 and 8, or a portion thereof. Still another embodiment of the present invention comprises treating allergically mediated inflammation in a mammal comprising, administering to the epidermis of the mammal, an effective amount at least one oligonucleotide, wherein said oligonucleotide comprises a sequence selected from the group consisting of: SEQ ID NOs: 5, 7 and 8 or portion thereof.

As described herein, the oligonucleotides of the present invention are easily administered to cells of interest using known methods of administration. The oligonucleotides of the present invention have measurable UV-mimetic activity in vivo that reasonably corresponds to UV-mimetic activity in vitro.

DETAILED DESCRIPTION OF THE INVENTION

Figure 1:
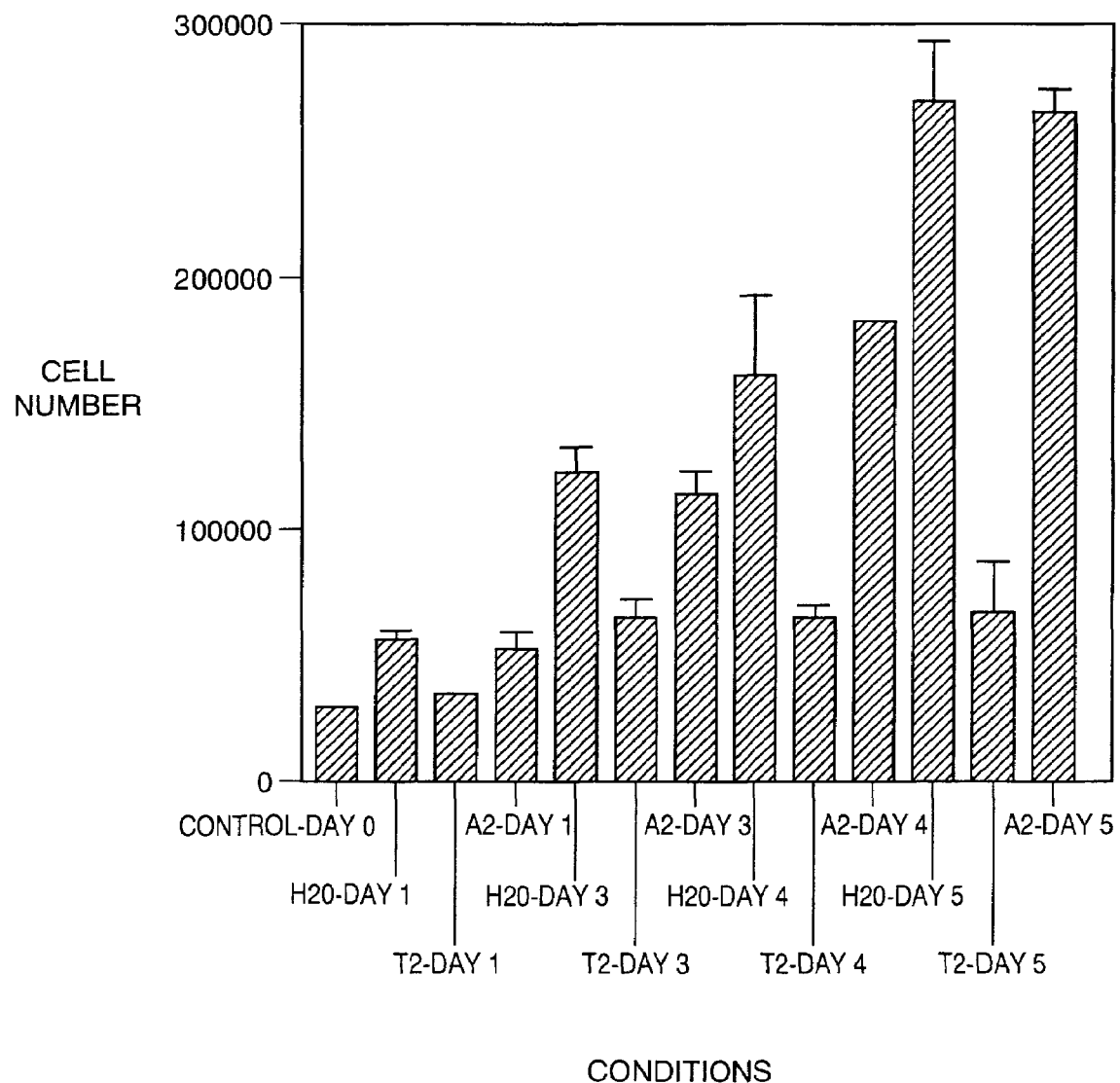
FIG. 1 is a graphic representation of the cell growth rate of human squamous carcinoma cells dosed with water (diluent), 100 μM pTpT (T$_2$) or 100 μM pdApdA (A$_2$), where day 0 is before dosage and days 1, 3, 4 and 5 are days after dosage.

The present invention is based on applicants' discovery that treatment of cells with DNA fragments, oligonucleotides or similar compounds can inhibit cell proliferation, or induce DNA repair or elicit a protective response to subsequent exposure to UV-irradiation or chemicals. It is likely that pTpT, other oligonucleotides and similar compounds, mimic the products of DNA damage or processed DNA-damage intermediates. pTpT evokes a melanogenic (tanning) response in skin (U.S. Pat. No. 5,643,556, the teachings of which are incorporated herein in their entirety), thus recapitulating the melanogenic protective response to UV irradiation. In the present invention, pTpT, other oligonucleotides and similar compounds are shown to induce the p53 pathway, including up-regulation of p53 inducible genes involved in DNA repair, such as p21, proliferating cell nuclear antigen (PCNA) and xerodoma pigmentosum group A protein (XPA). In one embodiment, the compounds of the present invention mimic compounds that induce the DNA damage signal, resulting in induction of the nucleotide excision repair pathway and transient cellular growth arrest that permits more extensive DNA repair before cell division, in the absence of genotoxic stress.

In addition, as described herein, exposure of cells to telomeric DNA sequences homologous to the 3' telomere overhang (such as the 11 nucleotide sequence of SEQ ID NO: 5) induces UV-mimetic responses such as DNA damage response, apoptosis and melanogenesis.

Such "mimicry" is useful in chemoprotection from carcinogenesis. Specifically, the invention pertains to use of compound such as DNA fragments, polynucleotides, oligonucleotides, deoxynucleotides, dinucleotides, or dinucleotide dimers, or similar compounds as described below, or an agent that increases activity of p53 protein, for the inhibition of cell proliferation or induction of DNA repair. As used herein, inhibition of cell proliferation includes complete abrogation of cell division, partial inhibition of cell division and transient inhibition of cell division as measured by standard tests in the art and as described in the Exemplification. The invention also pertains to the prevention or treatment of certain hyperproliferative diseases and pre-cancerous conditions affecting cells such as epithelial cells, keratinocytes or fibroblasts. Diseases and conditions include skin diseases such as psoriasis and hyperproliferative, pre-cancerous or UV-induced dermatoses such as contact dermatitis in mammals, and particularly in humans. The invention further pertains to use of the compounds of the present invention to reduce of photoaging (a process due in part to cumulative DNA damage), reduce oxidative stress and oxidative damage. The invention also pertains to prophylaxis against or reduction in the likelihood of the development of skin cancer in a mammal. In addition, the compounds of the present invention can be used to induce apoptosis in cells such as cells that have sustained genetic mutation, such as malignant or cancer cells or cells from an actinic keratosis. The invention further provides compositions comprising said compounds.

All types of epithelial cells are expected to respond to the method of the present invention as demonstrated by the representative in vitro and in vivo examples provided herein. Epithelial cells suitable for the method of the present invention include epidermal cells, respiratory epithelial cells, nasal epithelial cells, oral cavity cells, aural epithelial cells, ocular epithelial cells, genitourinary tract cells and esophageal cells, for example. Gastrointestinal cells are also contemplated; as described herein, methods of modifying or derivatizing nucleotide containing polymers such that they are resistant to degradation, for example by endo and exonucleases, are well known in the art.

Cells that contain damaged or mutated DNA include, for example, actinic keratosis cells, skin cancer cells and cells that have been exposed to DNA damaging chemicals or conditions. As described herein, allergically mediated inflammation includes conditions such as atopic dermatitis, contact dermatitis, allergic rhinitis and allergic conjunctivitis.

In one embodiment, the compounds of the present invention comprise DNA fragments of approximately 2–200 bases in length, deoxynucleotides (single bases), dinucleotides, or dinucleotide dimers, are administered to the mammal (e.g., human) in an appropriate vehicle. In another embodiment, the DNA fragments or oligonucleotides are about 2 to about 20 nucleotides in length. In still another embodiment, the DNA fragments or oligonucleotides are about 5 to about 11 nucleotides in length. As used herein, "DNA fragments" refers to single-stranded DNA fragments, double-stranded DNA fragments, or a mixture of both single- and double-stranded DNA fragments. "Deoxynucleotides" refers to either a single type of deoxynucleotide or a mixture of different deoxynucleotides. "Dinucleotides" can comprise a single type of nucleotide or different types of nucleotides, and can comprise a mixture of different types of dinucleotides. In one embodiment, the nucleotides of the dinucleotides are deoxynucleotides. Representative dinucleotides include $d(pT)_2$, $d(pC)_2$, $d(pA)_2$, $d(pCpT)$, $d(pTpC)$, $d(CpT)$, $d(TpC)$ and $d(TpT)$, where T is thymine, C is cytosine, d is deoxy, and p is phosphate (see Niggli, *Photochem. Photobiol.* 38(3):353–356 (1988)).

It is understood that other base-containing sequences can also be used in the present invention, where bases are, for example, adenine, thymine, cytosine, guanine or uracil. As described below, the bases or the backbone of the oligonucleotide can be modified or dervitized. In one embodiment, the oligonucleotides of the present invention comprise a 5' phosphate. A combination of one or more of compounds of the present invention can also be used. The DNA fragments, oligonucleotides, deoxynucleotides, or dinucleotides can be ultraviolet-irradiated. Such ultraviolet irradiation results in photodimerization between two adjacent pyrimidine residues (i.e., thymine (T) and cytosine (C)) present in the DNA fragments or dinucleotides.

As shown herein, the DNA fragments oligonucleotides and dinucleotides of the present invention exhibited UV mimetic activity such as inhibition of proliferation, melanogenesis, TNFα production and induction of apoptosis in cells, when the cells were contacted with the DNA fragments oligonucleotides and nucleotides of the present invention. For example, thymidine dinucleotide (pTpT) inhibits proliferation of several human cell types including squamous cell carcinoma, cervical carcinoma, melanoma, neonatal keratinocytes and normal neonatal fibroblasts (Examples 1–5, respectively). pTpT also reduced epidermal proliferation in vivo in a guinea pig model (Example 6). Furthermore, pTpT treatment of cells resulted in the nuclear localization of p53 (Example 7) and the induction of p53-regulated genes (Example 8) such as genes involved in DNA repair. Pretreatment of cells with pTpT enhanced their ability to repair DNA damaged by UV irradiation and by the chemical carcinogen benzo(a)pyrene (Examples 8 and 9). This repair occurs at least in part through activation of p53 and up-regulation of genes transcriptionally activated by p53, such as the p21/Waf/Cip 1 gene. Pretreatment of mouse skin with pTpT also resulted in a reduced level of UV-induced mutation in vivo (Example 14).

Thymidine dinucleotide, pTpT, mimics some effects of UV light including inducing melanogenesis and stimulating keratinocyte production of TNFα (Example 4). pTpT also induces TNFα and reduces contact hypersensitivity in vivo (Example 10). UVB radiation is a potent inhibitor of the inductive phase of contact hypersensitivity (CH), and TNFα is a mediator of this suppressive effect. Thymidine dinucleotides (pTpT), a substrate for UV-induced thymine dimer formation, simulates several UVB effects including increased tyrosinase expression and melanin content in cultured melanocytes and skin tanning in guinea pigs. Adenine dinucleotides (PApA), less commonly dimerized by UV, are much less effective. As shown in Example 10, the compounds of the present invention also mimic the suppressive effect of UVB on contact hypersensitivity in a mouse model. As demonstrated by the present invention, intracutaneous injection or topical application of pTpT can inhibit the induction of contact hypersensitivity and can activate the TNFα gene in vivo.

Example 10 also demonstrates that pTpT induces production of IL-10 mRNA and protein which is active in inhibiting T cell proliferation in allogenic mixed lymphocyte assay. In human skin, IL-10 as well as TNFα induce specific tolerance for contact hypersensitivity and delayed-type hypersensitivity reactions. Therefore, the DNA fragments, oligonucleotides, deoxynucleotides, dinucleotides and dinucleotide dimers of the present invention are reasonably expected to have immunosuppressive effects in vivo, e.g., to inhibit contact hypersensitivity and delayed-type hypersensitivity. These findings expand the spectrum of UVB effects mimicked by the compounds of the present invention.

In further examples of the UV mimetic activity of the DNA fragments of the present invention, a nine-nucleotide oligomer, GAGTATGAG (SEQ ID No: 1) stimulated melanogenesis in human melanocytes and induced the expression of p21/Waf/Cip 1 in a squamous cell carcinoma cell line. Furthermore, a scrambled version of the 9-mer, TAGGAGGAT (SEQ ID NO: 2), and truncated versions of the original 9-mer, AGTATGA (SEQ ID NO: 3), and GTATG (SEQ ID NO: 4), also stimulated melanogenesis in human melanocytes (Example 11). In addition, the sequence GTTAGGGTTAG (SEQ ID NO: 5) stimulated pigmentation in Cloudman S91 melanoma cells (Example 12) and induced apoptosis in a human T-cell line (Example 13). As demonstrated herein, SEQ ID NO: 5 induced human T cells to undergo apoptosis, while SEQ ID NOs: 9 and 10 did not significantly increase apoptosis in these cells (Example 13). SEQ ID NOs: 6–12 demonstrate at least some ability to induce melanogenesis (Examples 11–13). As described herein, the in vitro UV mimetic activities of the compounds of the present invention correlate with in vivo activity. In one embodiment, pTpT and SEQ ID NO: 1 treatment of mouse skin results in a 70% and 250% increase in melanin production, respectively (Example 12). Taken together, like pTpT, these oligonucleotides induce a broad range of UV mimetic activity both in vitro and in vivo upon contacting cells of interest with the oligonucleotide.

As demonstrated herein, oligonucleotides as small as dinucleotides (e.g. pTpT) and oligonucleotides of about 20 nucleotides in length can also be used. In another embodiment, oligonucleotides of about 11 nucleotides can be used. In still another embodiment, oligonucleotides of 5' nucleotides in length can be used to penetrate the skin barrier and effectively induce melanogenesis, inhibit cell growth and induce immunosuppression. Furthermore, these results demonstrate that the in vitro effects of these compounds also occur in vivo upon contacting the cells or tissue of interest with the compounds of the present invention. For example, as demonstrated herein, for the effect of inhibition of cell proliferation, TNF-α production and melanin production, in vitro induction of these activities by the compounds of the present invention is predictive of the ability of these compounds to produce the same effects in vivo. Any suitable method of administering the compounds of the present invention to the organism, such that the compound contacts the cells or tissues of interest is reasonably expected to produce measurable UV mimetic effect. The effect can be optimized using routine optimization protocols.

The compounds of the present invention are therefore useful in methods of inhibiting cell proliferation, preventing cancer, photoaging and oxidative stress by enhancing DNA repair, and by enhancing pigmentation through increased melanin production. Melanin is known to absorb photons in the UV range and therefore its presence reduces the risk of cancer and photoaging.

The DNA fragments, oligonucleotides, deoxynucleotides, dinucleotides, or dinucleotide dimers can be obtained from any appropriate source, or can be synthetically produced. For example, salmon sperm DNA can be dissolved in water, and then the mixture can be autoclaved to fragment the DNA. In one embodiment, the DNA fragments, oligonucleotides, deoxynucleotides, dinucleotides or dinucleotide dimers contain a 5' phosphate.

The compounds of the present intention also play a protective role in UVA-induced oxidative damage to the cell (Example 15). As described in Example 15, primary newborn fibroblasts treated with 10 μM pTpT for 3 days and then stimulated with $5 \times 10^{-5}$ or $5 \times 10^{-4} H_2O_2$ had higher cell yields compared to diluent treated controls. Analysis of mRNA and protein revealed that in pTpT treated cells, Cu/Zn superoxide dismutase was elevated. This enzyme participates in the process of oxygen radical quenching. Thus, in one embodiment of the present invention, the compounds of the present invention are administered to cells to protect against oxidative damage. In one embodiment, these compounds are topically administered to the epidermis of an individual.

An "agent that increases activity of p53 protein," as used herein, is an agent (e.g., a drug, molecule, nucleic acid fragment, or nucleotide) that increases the activity of p53 protein and therefore results in increase in an DNA repair mechanisms, such as nucleotide excision repair, by the induction of proteins involved in DNA repair, such as PCNA and the XPA mutated protein. The activity of p53 protein can be increased by directly stimulating transcription or translation of p53 DNA or RNA; by increasing expression or production of p53 protein; by increasing the stability of p53 protein; by increasing the resistance of p53 mRNA or protein to degradation; by causing p53 to accumulate in the nucleus of a cell; by increasing the amount of p53 present; or by otherwise enhancing the activity of p53. The p53 protein itself is also an agent that increases the activity of p53 protein. A combination of more than one agent that increases the activity of p53 can be used. Alternatively or in addition, the agent that increases the activity of p53 can be used in combination with DNA fragments, deoxynucleotides, or dinucleotides, as described above.

Ultraviolet irradiation produces DNA photoproducts that when not promptly removed, can cause mutations and skin cancer. Repair of UV-induced DNA damage requires efficient removal of the photoproducts to avoid incorporation of mutation during DNA replication. Age-association decrease in DNA repair capacity is associated with decreased constitutive levels of p53 and other nuclear excision repair (NER) proteins required for removing UV-induced photoproducts. As demonstrated herein, compounds of the present invention induced NER proteins in human dermal cells when these cells were treated with these compounds before UV irradiation (Example 16). While there were age related decreases in NER proteins, NER proteins in cells from donors of all ages from newborn to 90 years were induced by 200–400%. A significant decrease in the rate of repair of thymine dimers and photoproducts occurs with increased age of cell sample; however, cells that were pre-treated with compounds of the present invention, then UV irradiated, removed photoproducts 30 to 60 percent more efficiently. Thus, the treatment of cells with small DNA oligonucleotides partially compensates for age-associated decreases in DNA repair capacity. In light of the in vivo efficacy of the compounds of the present invention, it is reasonable to expect that treatment of human skin with the compounds of the present invention enhances endogenous DNA repair capacity and reduces the carcinogenic risk from solar UV irradiation. This method is especially useful in older individuals who likely have reduced cellular DNA repair capacity.

The DNA fragments, deoxynucleotides, oligonucleotides dinucleotides or dinucleotide dimers, or agents that increase the activity of p53 protein, can be administered alone or in combination with physiologically acceptable carriers, including perfumes or colorants, stabilizers, sunscreens or other ingredients, for medical or cosmetic use. They can be administered in a vehicle, such as water, saline, or in another appropriate delivery vehicle. The delivery vehicle can be any appropriate vehicle which delivers the DNA fragments, oligonucleotides, deoxynucleotides, dinucleotides, or dinucleotide dimers, or agent that increases the activity of p53 protein. In one embodiment, propylene glycol is used as a delivery vehicle. In a preferred embodiment, a mixture of propylene glycol:ethanol:isopropyl myristate (1:2.7:1) containing 3% benzylsulfonic acid and 5% oleyl alcohol is used. In another embodiment, a liposome preparation is used. The liposome preparation can be comprised of any liposomes which penetrate the cells of interest or the stratum corneum and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used.

In one embodiment, the DNA fragments, oligonucleotides, deoxynucleotides, dinucleotides, or dinucleotide dimers, or agent that increases p53 activity, are applied topically to the skin surface. In other embodiments, the DNA fragments, oligonucleotides, deoxynucleotides, dinucleotides, or dinucleotide dimers, or agent that increases p53 activity, are delivered to other cells or tissues of the body such as epithelial cells. Cells on tissue that are recognized to have a lesser barrier to entry of such substances than does the skin can be treated, e.g., orally to the oral cavity; by aerosol to the respiratory epithelium; by instillation to the bladder epithelium; by instillation or suppository to intestinal (epithelium) or by other topical or surface application means to other cells or tissues in the body, including eye drops, nose drops and application using angioplasty, for example. Furthermore, the oligonucleotides of the present invention can be administered intravenously or injected directly into the tissue of interest intracutaneous, subcutaneously, intramuscularly or intraperitoncally. In addition, for the treatment of blood cells, the compounds of the present invention can be administered intravenously or during extracorporeal circulation of the cells, such as through a photophoresis device, for example. As demonstrated herein, all that is needed is contacting the cells of interest with the oligonucleotide compositions of the present invention wherein the oligonucleotides contacting the cells can be as small as dinucleotides.

The DNA fragments, oligonucleotides, deoxynucleotides, dinucleotides, or dinucleotide dimers, or agent that increases p53 activity, are administered to (introduced into or contacted with) the cells of interest in an appropriate manner. The "cells of interest", as used herein, are those cells which may become affected or are affected by the hyperproliferative disease or precancerous condition, or cells which are affected by oxidative stress, DNA-damaging conditions such as UV irradiation or exposure to DNA damaging chemicals such as benzo(a)pyrene. Specifically encompassed by the present invention are epithelial cells, including melanocytes and keratinocytes, as well as other epithelial cells such as oral, respiratory, bladder and cervical epithelial cells. As demonstrated herein, the methods and compositions of the present invention inhibit growth, induce melanogenesis and induce TNFα production in epithelial cells from numerous sources.

The DNA fragments, deoxynucleotides, dinucleotides, or dinucleotide dimers, or agent that increases p53 activity, are applied at an appropriate time, in an effective amount. The "appropriate time" will vary, depending on the type and molecular weight of the DNA fragments, deoxynucleotides, dinucleotides, or dinucleotide dimers, or agent, employed; the condition to be treated or prevented; the results sought; and the individual patient. An "effective amount", as used herein, is a quantity or concentration sufficient to achieve the desired result. The effective amount will depend on the type and molecular weight of the DNA fragments, deoxynucleotides, dinucleotides, or dinucleotide dimers, or agent, employed; the condition to be treated or prevented; the results sought; and the individual patient. For example, for the treatment or prevention of psoriasis, or for hyperproliferative, pre-cancerous, or UV-induced dermatoses, the effective amount is the amount necessary to relieve any one of the symptoms of the disease, to reduce the area of skin affected by the disease, or to prevent the formation of affected areas. The concentration will generally be approximately 2–300 µM. In a another embodiment, the concentration is about 50–200 µM; in another embodiment, the concentration is about 75–150 µM. It is understood that modification of the oligonucleotides of the present invention to prevent their degradation, prolong their half life in the body or increase their uptake into cells would allow the use of less oligonucleotide and/or lower concentrations of oligonucleotide, concentration of 0.1–1.0 µM, for example.

In one embodiment of the present invention, DNA fragments, such as single-stranded DNA fragments, deoxynucleotides, dinucleotides, or dinucleotide dimers, or an agent that increases p53 activity, are administered, either without a vehicle or in an appropriate delivery vehicle, to the cells of interest in the mammal in order to treat or prevent a hyperproliferative disease affecting epithelial cells. The DNA fragments, oligonucleotides, deoxynucleotides, dinucleotides, or dinucleotide dimers, or agent that increases p53 activity, can be administered directly to affected areas, or can be applied prophylactically to regions commonly affected by the hyperproliferative disease.

In another embodiment of the invention, the DNA fragments, oligonucleotides, deoxynucleotides, dinucleotides, or dinucleotide dimers, or agent that increases p53 activity, are administered, either without a vehicle or in an appropriate delivery vehicle, to the epidermis for the treatment or prevention of psoriasis. The DNA fragments, oligonucleotides, deoxynucleotides, dinucleotides, or dinucleotide dimers, or agent that increases p53 activity, can be administered topically or by subcutaneous injection directly to affected areas, or can be applied prophylactically to regions of epidermis commonly affected.

In another embodiment of the invention, the DNA fragments, oligonucleotides, deoxynucleotides, dinucleotides, or dinucleotide dimers, or agent that increases p53 activity, are administered, either without a vehicle or in an appropriate delivery vehicle, to the epidermis for the treatment or prevention of atopic dermatitis, contact dermatitis (e.g., contact hypersensitivity) or allergically mediated inflammation of other epithelial cells such as allergic rhinitis or allergic conjunctivitis (hayfever) in a mammal. The DNA fragments, oligonucleotides, deoxynucleotides, dinucleotides, or dinucleotide dimers, or agent that increases p53 activity, can be administered topically or by intracutaneous injection directly to affected areas, or can be applied prophylactically to regions of epidermis commonly affected. In another embodiment, the DNA fragments, oligonucleotides, deoxynucleotides, dinucleotides, or dinucleotide dimers, or agent that increases p53 activity are administered to a region of the epidermis that is distinct from the affected region. As demonstrated in Example 10, the treatment of abdominal skin resulted in inhibition of contact hypersensitivity at the ear in a mouse model for contact hypersensitivity.

In another embodiment of the invention, the DNA fragments, oligonucleotides, deoxynucleotides, dinucleotides, or dinucleotide dimers, or agent that increases p53 activity, are administered, either alone or in an appropriate delivery vehicle, to the epidermis for the treatment or prevention of vitiligo. The DNA fragments, oligonucleotides, deoxynucleotides, dinucleotides, or dinucleotide dimers, or agent that increases p53 activity, can be administered topically on intracutaneous injection directly to affected areas, or can be applied prophylactically to regions of epidermis commonly affected.

In another embodiment, DNA fragments, oligonucleotides, deoxynucleotides, dinucleotides, or dinucleotide dimers, or agent that increases p53 activity, are administered, either alone or in an appropriate delivery vehicle, to the epidermis for the treatment or prevention of oxidative stress or for the treatment or prevention of hyperproliferative, pre-cancerous or UV-responsiveness dermatoses.

In a still another embodiment, DNA fragments, oligonucleotides, deoxynucleotides, dinucleotides, or dinucleotide dimers, or an agent that increases p53 activity, are administered, either alone or in an appropriate delivery vehicle, to the epidermis for reduction of photoaging, or prophylaxis against or reduction in the likelihood of development of skin cancer. The DNA fragments, oligonucleotides, deoxynucleotides, dinucleotides, or dinucleotide dimers, or agent that increases p53 activity, are administered topically or by intracutaneous injection at an appropriate time (i.e., sufficiently close in time to exposure of the skin to UV irradiation). The DNA fragments, oligonucleotides, deoxynucleotides, dinucleotides, or dinucleotide dimers can be applied before, during or after exposure to UV irradiation. They can be applied daily or at regular or intermittent intervals. In one embodiment, the DNA fragments, oligonucleotides, deoxynucleotides, dinucleotides, or dinucleotide dimers, or agent that increases p53 activity, can be administered on a daily basis to skin which may be exposed to sunlight during the course of the day.

In a further embodiment of the invention, the DNA fragments oligonucleotides, deoxynucleotides, dinucleotides, or dinucleotide dimers, or agent that increases p53 activity, are administered, either without a vehicle or in an appropriate delivery vehicle, to an individual (e.g., epithelial cells of an individual) for the treatment or prevention of hyperproliferative, pre-cancerous conditions, or to repair or prevent DNA damage caused by DNA damaging chemicals, such as benzo(a)pyrene.

As demonstrated herein, the compounds of the present invention are active in vitro and in vivo in their unmodified form, e.g., sequences of unmodified oligonucleotides linked by phosphodiester bonds. However, these compounds can also be prepared or modified using techniques well known in the art to render these compounds resistant to degradation, e.g., by endo and exonucleases. For example, modification can include one or more modifications of the nucleotide subunits or portion thereof, e.g., the base, the sugar or the phosphate backbone. Useful modifications, for example, to the phosphate backbone include phosphorothioate, phosphorodithioate, phosphoamidate, methylphosphonate, and combinations thereof. The backbone can comprise a mixture of phosphate linkages, where the different linkages are dispersed through the chain, grouped in regions of the chain, at the ends of the chain, middle of the chain or combination thereof. Phosphorothioate has been studied in vitro and in vivo for uptake into cells as well as half-life in vivo (Iverson, P., *Anti-Cancer Drug Design*, (1991), 6531–6538 and *Antisense Research and Dev.* 4:43–52 (1994)). Phosphorothioate containing oligonucleotides showed no toxicity at potentially therapeutic concentrations of about 0.1–1.0 µM in several tissues in animal models (Agrawal et al., *Proc. Natl. Acad. Sci. USA*, 88:7595–7599 (1991)). Furthermore, the phosphodiester backbone can be replaced in whole or in part by one or more non-natural backbones, such as a peptide backbone. Therefore, the compounds of the present invention include oligomers of peptide nucleic acid (PNA), ribonucleic acid, deoxyribonucleic acid, chimeric oligomers or linked polymers. Chimeric oligomers comprise nucleic acid subunits of more than one type (e.g., DNA with RNA subunits, DNA with PNA subunits, RNA with PNA subunits or all three subunits). Linked polymers comprise oligomers of one type of subunit linked to an oligomer of the same or different subunit. Methods of linking oligomers comprising DNA, RNA or PNA are well known in the art. As used herein, the term oligonucleotide includes DNA, RNA, PNA, modified or derivitized versions thereof, chimeric and linked versions thereof.

As used herein, the term "Peptide Nucleic Acid" or "PNA" includes compounds referred to as Peptide Nucleic Acids in U.S. Pat. Nos. 5,539,082, 5,527,675, 5,623,049 or 5,714,331 (herein incorporated by reference). Further modifications of PNA are well known in the art. Furthermore, like DNA, the backbone of the PNA can be modified, for example, to comprise phosphono-PNA.

Furthermore, although not necessary for the ability to elicit the UV-mimetic effects of the present invention, the compound of the present invention can be modified, derivitized or otherwise combined with other reagents to increase the half life of the compound in the organism and/or increase the uptake of these compounds by the cells of interest. Modification reagents include, for example, lipids or cationic lipids. In one embodiment, the compounds of the present invention are covalently modified with a lipophilic group, an adamantyl moiety. The compounds of the present invention can be modified to target specific tissues in the body. For example, brain tissue can be targeted by conjugating the compounds with biotin and using the conjugated compounds with an agent that facilitates delivery across the blood-brain barrier, such as anti-transferrin receptor antibody coupled to streptavidin.

The invention is further illustrated by the following non-limiting Examples.

EXAMPLE 1

Application to Human Squamous Carcinoma Cells

Human squamous carcinoma cells line SCC12F cells were maintained in primary keratinocyte medium (300 ml DME, 100 ml F-12 nutrient supplement, 50 ml 10× Adenine, 50 ml fetal bovine serum, 5 ml penicillin/streptomycin stock, and 0.5 ml of 10 µg/ml epidermal growth factor and hydrocortisone to final concentration of 1.4 µg/ml) and dosed with either water (diluent), 100 µM pTpT ($T_2$, Midland Certified Reagent Company, Midland, Tex.) or 100 µM pdApdA ($A_2$). Cells were harvested before dosing (day 0), and 1,3,4, and 5 days after dosage, and were counted by COULTER™ counter. After harvesting, the cells were processed for total RNA isolation and were analyzed by Northern blot. Addition of pTpT to human squamous carcinoma cells resulted in marked decreases in cell growth rate, as shown in FIG. 1. Addition of a control deoxyadenine dinucleotide (pdApdA), a compound very similar to pTpT but not readily dimerized by UV irradiation and therefore rarely excised during the course of UV-induced DNA repair, has no effect.

Figure 2:
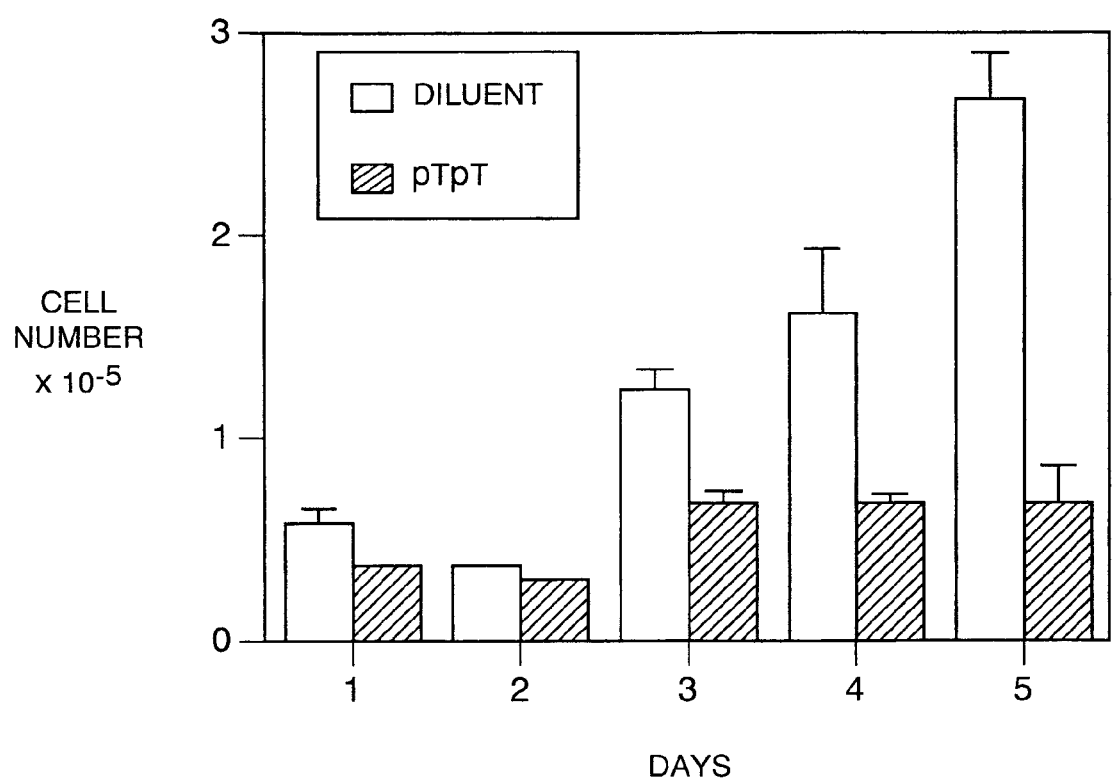
FIG. 2 is a graphic representation of the cell growth rate of normal human fibroblasts dosed with water (diluent) or 100 μM pTpT (T$_2$), where day 0 is before dosage and days 1, 3, 4 and 5 are days after dosage and where values represent averages±standard deviations of duplicate cultures.

In a second experiment, SCC12F cells were cultured as described above. Two or three days after seeding, the preconfluent cultures were given fresh medium supplemented with either 100 µM $T_2$ or diluent as a control. Cells were collected daily by trypsinization and counted by COULTER™ counter. The cell yield in cultures treated with $T_2$ was reduced by 75% compared to that of paired control cultures after five days (FIG. 2). This corresponds to 2.3 population doublings in this time for control cells, compared with 1 doubling for $T_2$-treated cells. These results further demonstrate that application of $AT_2$ DNA fragments inhibits cell proliferation, including proliferation of cancerous cells.

In a third experiment, it was demonstrated that addition of $T_2$ to human squamous carcinoma cells for 24–72 hours resulted in upregulation of at least three genes: growth arrest and DNA damage (GADD 45), senescence-derived inhibitor (Sdi I), and excision repair cross-complementing (ERCC-3). Paired cultures of SCC12F cells were maintained in a Dulbecco's modified Eagle's Medium (DMEM; GIBCO/ BRL, Gaithersburg, Md.)-based keratinocyte growth medium supplemented with 10% fetal calf serum (Hyclone Labs, Logan, Utah) and epidermal growth factor as described (Hollander, M. C. et al., *J. Biol. Chem.* 268: 328–336 (1992)). Pre-confluent cultures were given fresh medium supplemented with either 100 µM $T_2$, or an equal volume of diluent. Cells were collected daily after additions and processed for total RNA isolation using the Tri-Reagent extraction method (Molecular Research Center, Cincinnati, Ohio) following the protocol of the manufacturer. Ten micrograms of RNA from each sample was gel electrophoresed, transferred to a nylon filter and probed as described previously (Nada, A. et al., *Exp. Cell Res.* 211:90–98 (1994)). The cDNA for GADD 45 was generated by PCR using primers based on the human GADD 45 gene sequence (Mitsudomi, T. et al., *Oncogene* 7:171–180 (1992)). The cDNA for ERCC 3 was purchased from the AMERICAN TYPE CULTURE COLLECTION (ATCC, Rockville, Md.). The SDI 1 cDNA was a gift of Dr. J. Smith and has been described previously (Walworth, N. C. and Bemards, R., *Science* 271:353–356 (1996)).

Compared to the diluent control, the mRNAs for GADD 45, ERCC 3 and SDI 1 were up-regulated in $T_2$-treated cells as early as 24 hours, and remained elevated for several days. Addition of the control $A_2$ was less effective or ineffective in inducing these genes. Comparable data have been obtained in experiments with S91 melanoma cells, and normal human fibroblasts.

The time course of induction is similar to that observed after UV irradiation for the two genes for which this has been studied (GADD 45 and Sdi I) and also similar to the time course of induction of the tyrosinase gene by $T_2$ in melanocytes and melanoma cells. Sdi I is known to be involved in cell cycle regulation and specifically in blocking cell division. GADD 45 and ERCC-3, a human DNA repair enzyme, are known to be involved in repair of UV-induced DNA damage. The response to $T_2$ is identical to that observed after UV irradiation of these cell lines, and is also similar to the response to various antimetabolites, such as methotrexate, that are clinically effective in the treatment of hyperproliferative skin disorders.

EXAMPLE 2

Application to Human Cervical Carcinoma Cells

Human cervical carcinoma cells (HeLa cells) were maintained in DME+10% calf serum and dosed with either water (diluent) or 100 µM $T_2$. Cells were collected 1, 4 and 6 days after dosage and counted by COULTER™ counter.

Figure 3:
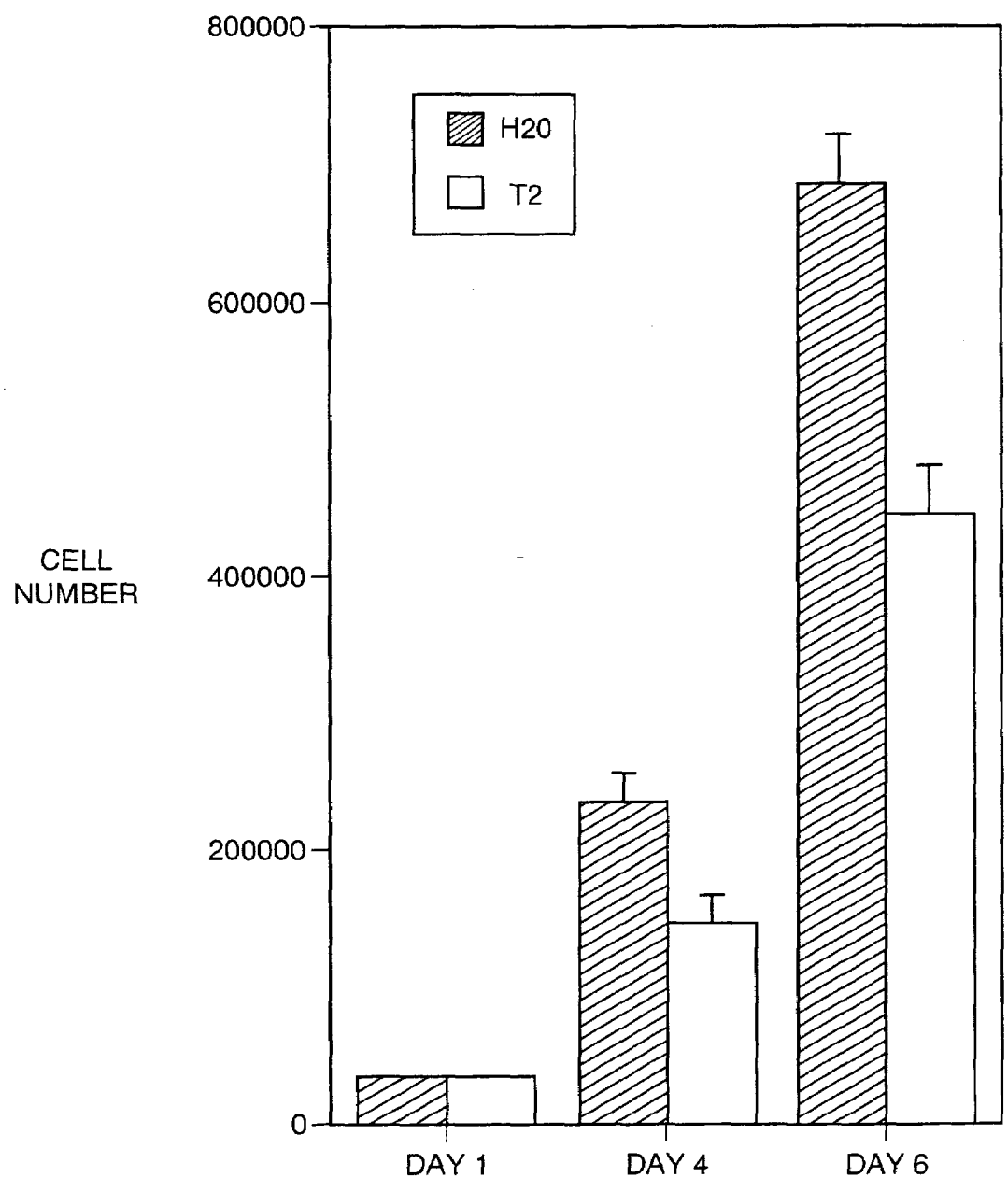
FIG. 3 is a graphic representation of the cell growth rate of human cervical carcinoma cells dosed with either water (diluent) or 100 μM pTpT (T$_2$), where day 0 is before dosage and days 1, 4 and 6 are days after dosage.

Addition of $T_2$ to the human cervical carcinoma cells resulted in marked decreases in cell growth rate, as shown in FIG. 3.

EXAMPLE 3

Application to Human Melanoma Cells

Human melanoma cell lines CRL 1424, Malma, Sk Mel 2, and Sk Mel 28 were obtained from the Collection AMERICAN TYPE CULTURE COLLECTION (ATCC). The cell lines were maintained in DME+2% calf serum, and dosed with either water (diluent) with DME, or 100 µM $T_2$ in DME. One week after dosage, cells were collected and counted by COULTER™ counter.

Figure 4:
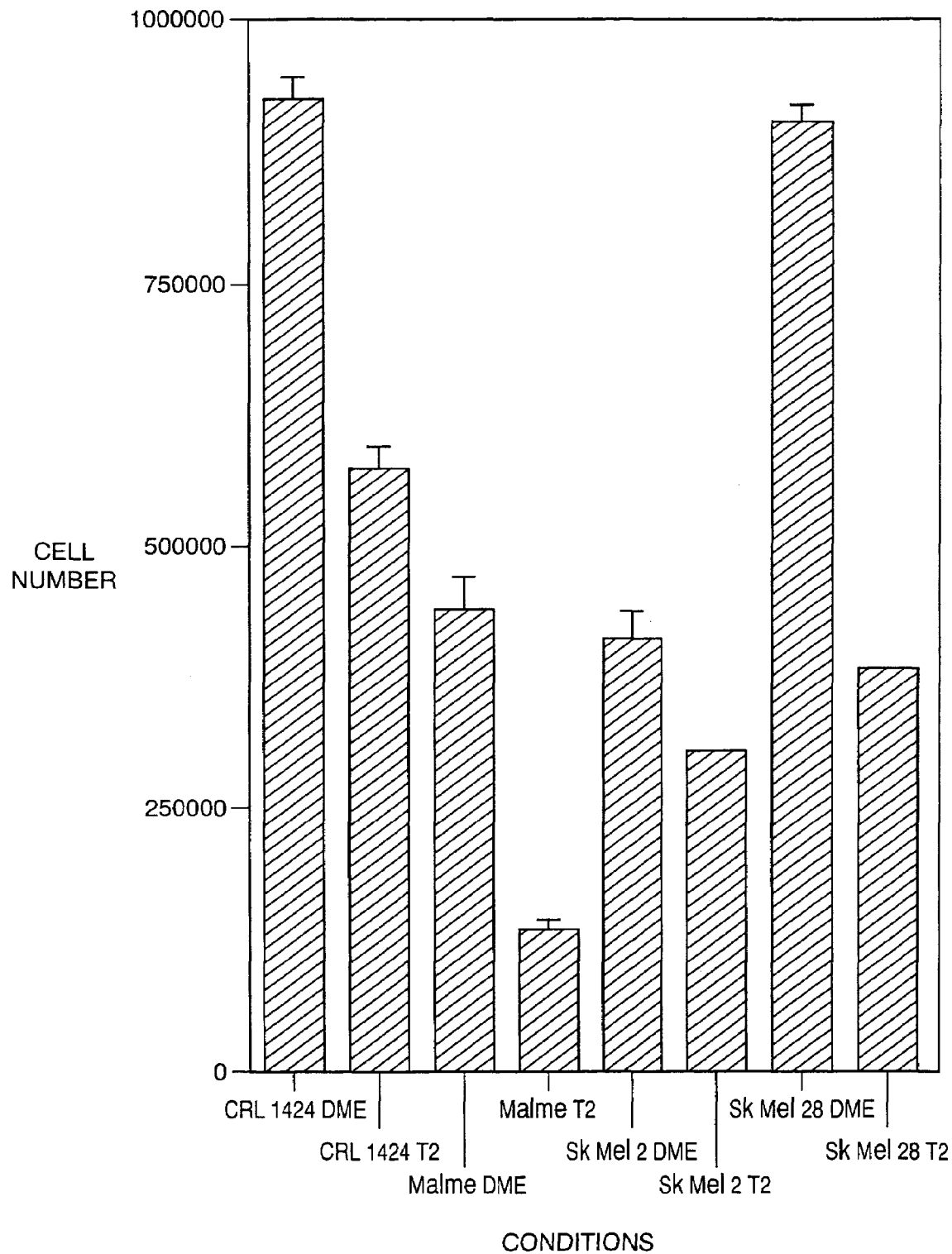
FIG. 4 is a graphic representation of the cell yield of human melanoma cell lines dosed with either diluent or 100 μM pTpT (T$_2$).
Figure 5:
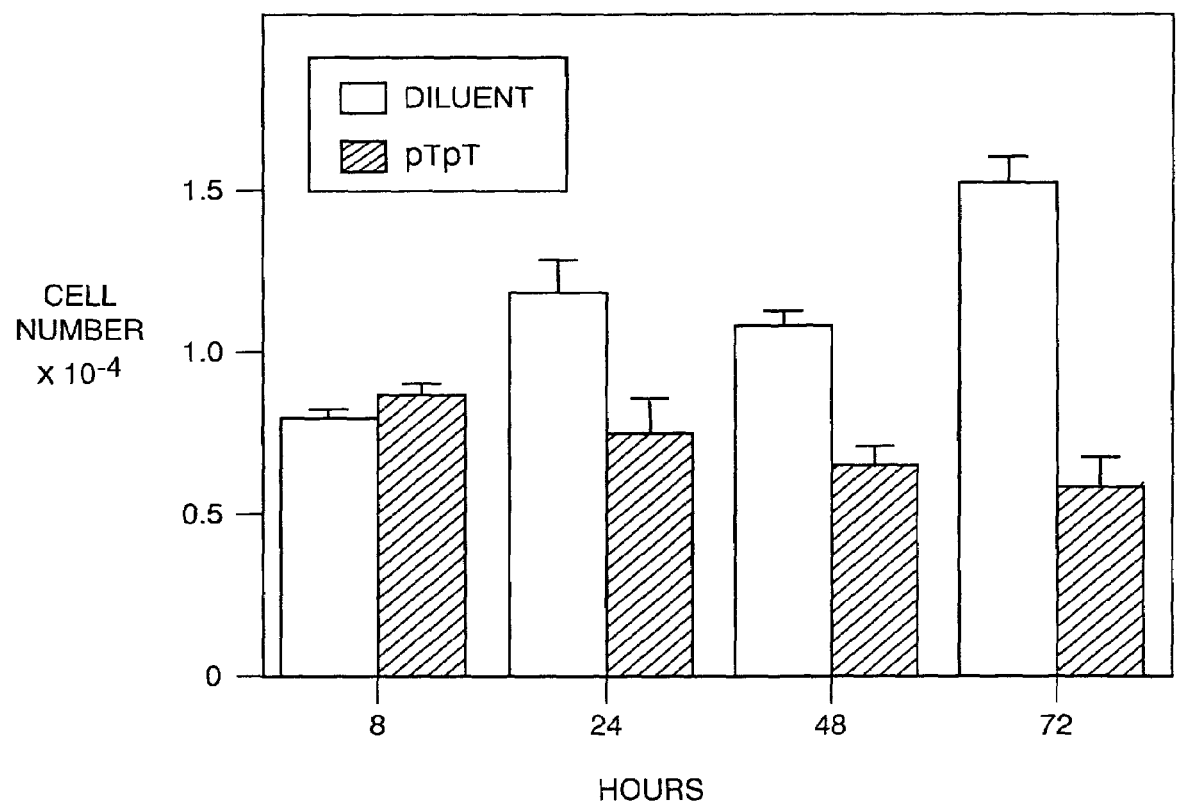
FIG. 5 is a graphic representation of the cell growth rate of normal human keratinocytes dosed with water (diluent) or 100 μM pTpT (T$_2$), where day 0 is before dosage and 8, 24, 48 and 72 are hours after dosage and where values represent averages±standard deviations of duplicate cultures.

Addition of $T_2$ to any of the four different human melanoma cell lines results in marked decreases in cell yields, as shown in FIG. 4.

EXAMPLE 4

Application to Human Keratinocytes

Figure 6:
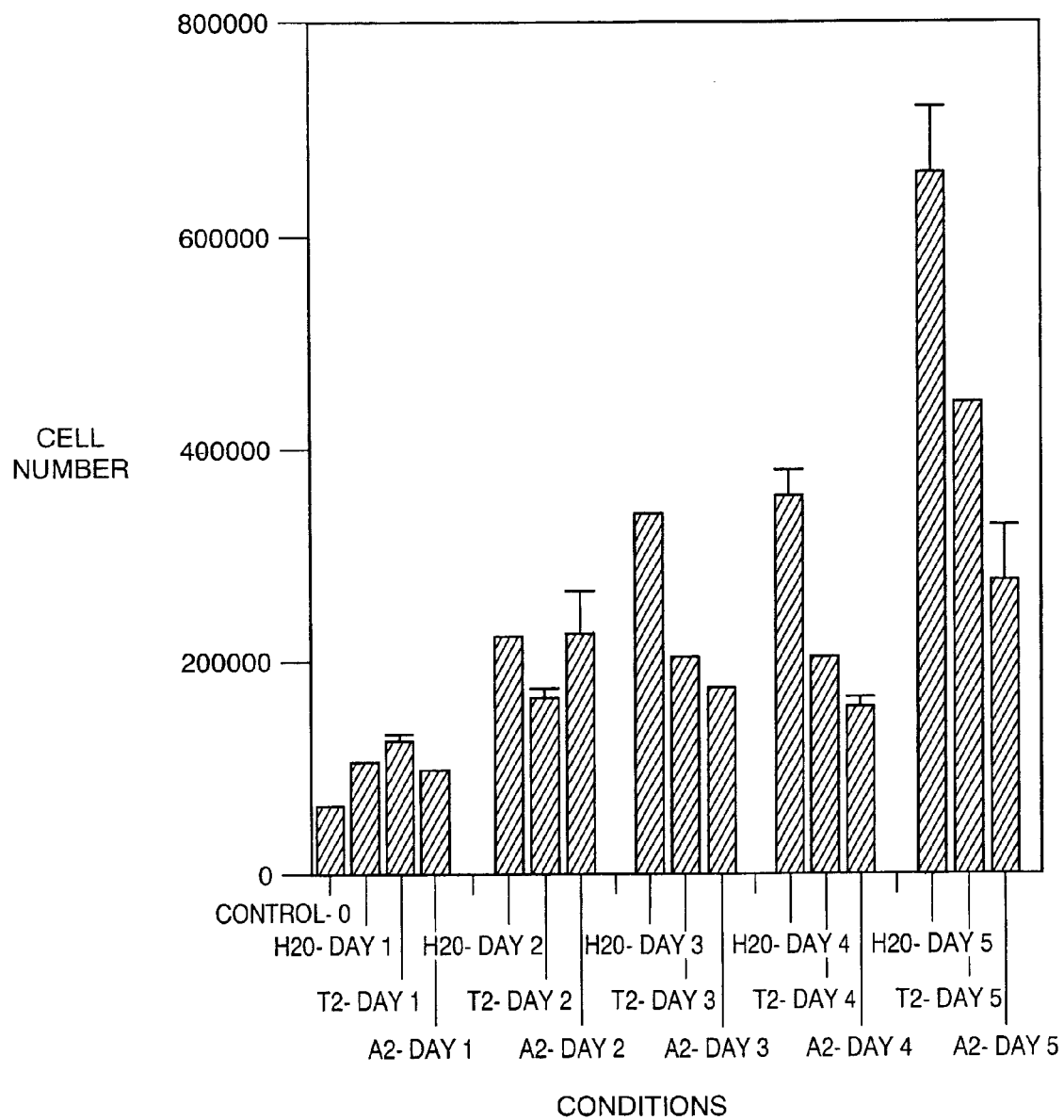
FIG. 6 is a graphic representation of the average cell number of human neonatal fibroblasts dosed with either water, T$_2$ or A$_2$.
Figure 7:
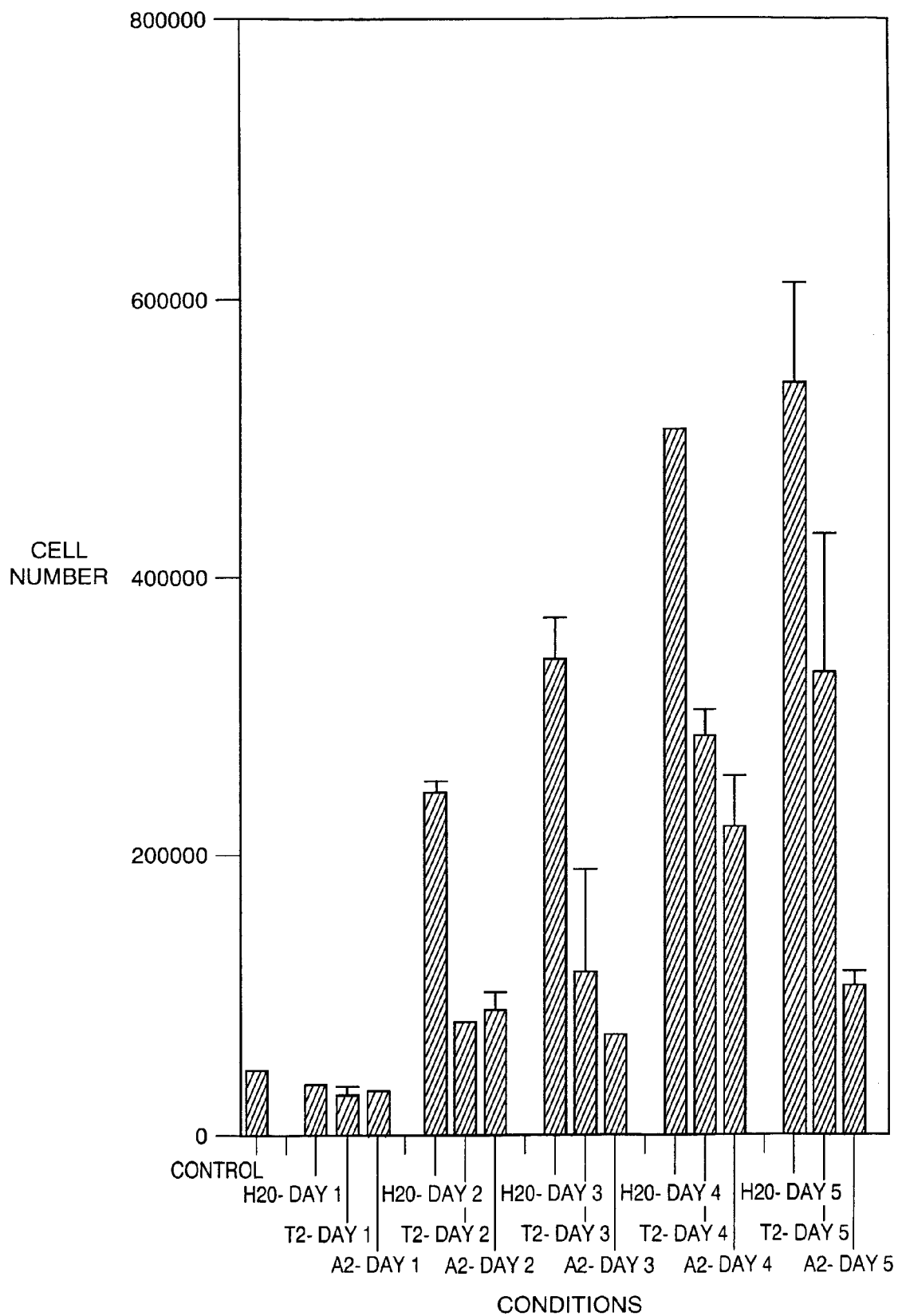
FIG. 7 is a graphic representation of the average cell number of human neonatal fibroblasts dosed with either water, T$_2$ or A$_2$.

Normal human neonatal fibroblasts were plated in Falcon P35 culture dishes at a density of $9 \times 10^4$ cells/dish. The culture medium was DME+10% calf serum, 2 ml per plate. One day after plating, cultures were supplemented with either 100 µM $T_2$ in DME or 100 µM $A_2$ in DME, or water (control). Two plates were collected and counted before the additions to give a starting, or "day 0," reading. Duplicate plates of each condition were harvested through five days after addition of the supplements and cell number determined. All cell counts were done by COULTER™ Counter. Results of two experiments, are shown in FIGS. 6 and 7. The results indicate that application of the DNA fragments inhibits cell proliferation.

Northern blot analysis of the normal human keratinocytes treated with $T_2$ for 24–72 hours that showed induction of the tumor necrosis factor alpha gene (TNFα). This immunomodulatory cytokine, known to be induced by UV irradiation, may thus be induced by $T_2$. Use of locally applied DNA fragments, deoxynucleotides, dinucleotides, or dinucleotide dimers is useful in immunodulation of cutaneous reactions and in treatment or prevention of diseases or conditions involving immune mediators.

EXAMPLE 5

Inhibition of Cell Growth of Normal Neonatal Fibroblasts by DNA Fragments

Normal human neonatal fibroblasts were plated in Falcon P35 culture dishes at a density of $9 \times 10^4$ cells/dish. The culture medium was DME+10% calf serum, 2 ml per plate. One day after plating, cultures were supplemented with either 100 µM $T_2$ in DME or 100 µM $A_2$ in DME, or water (control). Two plates were collected and counted before the additions to give a starting, or "day 0," reading. Duplicate plates of each condition were harvested through five days after addition of the supplements and cell number determined. All cell counts were done by Coulter™ Counter. Results of two experiments, are shown in FIGS. 6 and 7. The results indicate that application of the DNA fragments inhibits cell proliferation.

Figure 8:
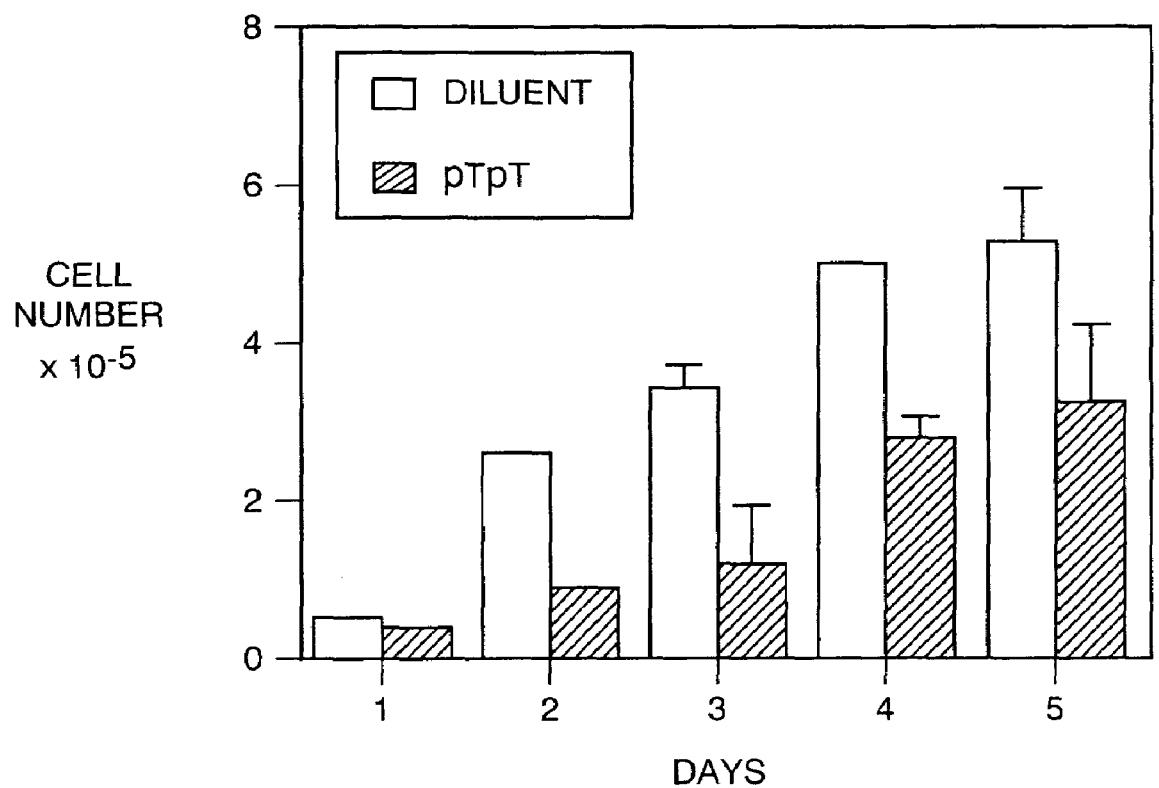
FIG. 8 is a graphic representation of the cell growth rate of normal human fibroblasts dosed with water (diluent) or 100 μM pTpT (T$_2$), where day 0 is before dosage and where values represent averages±standard deviations of duplicate cultures.

In a second experiment, normal human neonatal fibroblasts were plated and cultured, as described above in Example 1 for SCC12F cells. Cultures were supplemented with either 100 µM $T_2$ or water (control), and cells were harvested for cell counts. The cell yield in fibroblast cultures treated with $T_2$ was reduced by 40% compared to that of paired control cultures after three days (FIG. 8). This corresponds to 4 population doublings in this time for control cells, compared with 3.6 doublings for $T_2$-treated cells. These results further demonstrate that contacting cells of interest with the DNA fragments of the present invention inhibits cell proliferation.

EXAMPLE 6

Effect of pTpT Applications on Epidermal Cell Proliferation

Guinea pigs received one or two daily topical applications of 100 µM pTpT, or vehicle alone as control, for three days. On the fourth day, punch biopsies were obtained and maintained for 7 or 8 hours in primary keratinocyte medium supplemented with 10 uCi/ml $^3$H-thymidine (specific activity 9.0 Ci/m mole, NEN). Proliferating cells are expected to incorporate the $^3$H-thymidine into newly synthesized DNA. Tissues were then rinsed with cold medium and fixed in 10% phosphate buffered formalin. After a series of dehydration steps, tissues were embedded in paraffin. 6 um sections were cut and mounted onto glass slides, dipped in NTB-2 Nuclear Track emulsion and kept in the dark at 4° C. for 7 days. Sections were developed in Kodak D-19 developer and stained with hematoxylin and eosin. Labeling index, a measure of DNA replication and therefore cell proliferation was measured by calculating the percentage of labeled nuclei among 100 basal keratinocytes.

Results:

| | Labeling Index 2 daily applications | |
|---|---|---|
| Vehicle control | | pTpT |
| 4 ± 1.4 | | 1.5 ± 0.7 |
| | 1 daily application | |
| Vehicle control | | pTpT |
| 4.5 ± 2.1 | | 2 ± 0 |

Results±SD are shown.

Labeling index (a measure of epidermal cell proliferation) is less in pTpT-treated skin than in vehicle-treated skin, (>0.03 paired T test) in both experiments. These results demonstrate that contacting cells of interest with the DNA fragments of the present invention inhibits cell proliferation.

EXAMPLE 7

Role of p53 in DNA Repair

Figure 9:
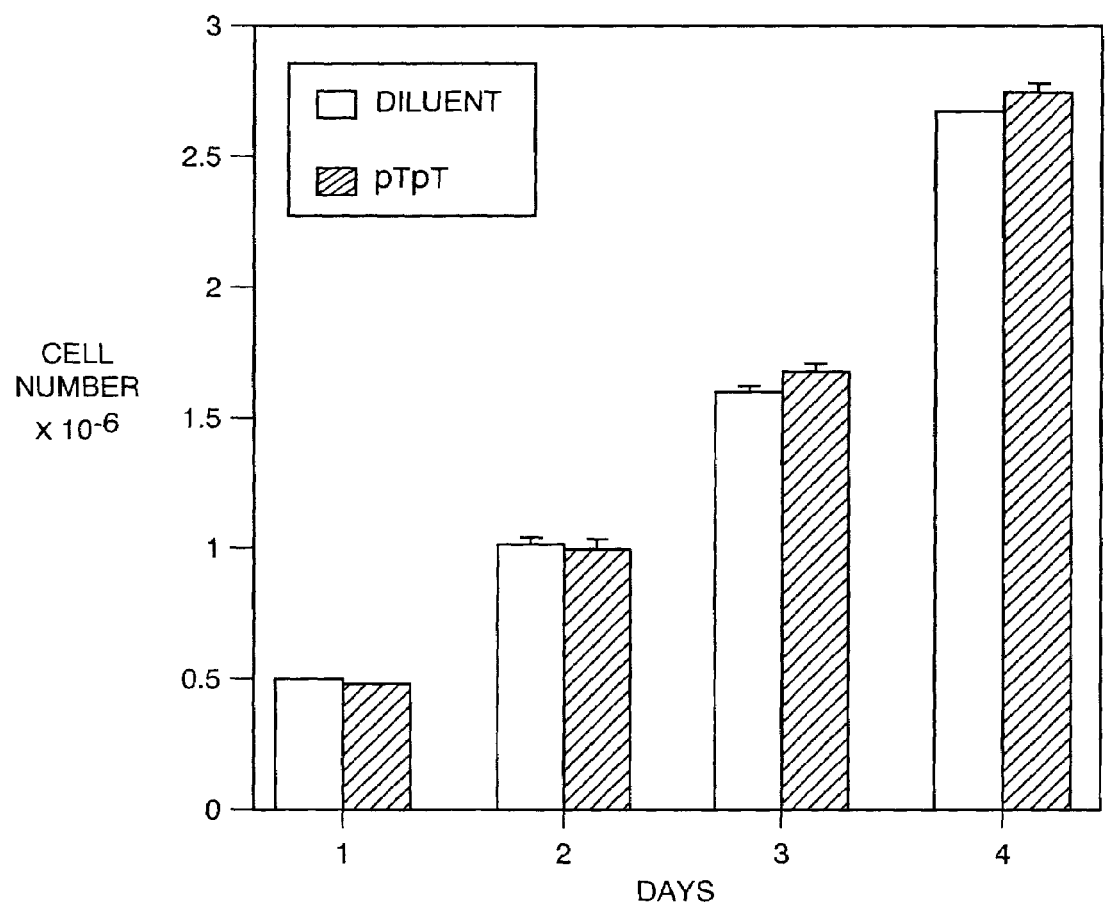
FIG. 9 is a graphic representation of the cell growth rate of p53-null H1299 lung carcinoma cells dosed with water (diluent) or 100 μM pTpT (T$_2$), where day 0 is before dosage and 1, 2, 3 and 4 are days after dosage, and where values represent averages±standard deviations of duplicate cultures.

Both the GADD 45 and SDI 1 genes are known to be transcriptionally regulated by the tumor suppressor protein p53. After UV and γ-irradiation, as well as treatment of cells with DNA-damaging chemical agents, there is a rapid stabilization and nuclear accumulation of p53 after which this protein binds to specific promoter consensus sequences and modulates the transcription of regulated genes. Recent data suggest that p53 can also be activated by the binding of small single-stranded DNAs, as well as certain peptides and antibodies, to a carboxyl terminal domain of this protein. In order to determine whether the inhibitory effect of the dinucleotide pTpT on cell proliferation is mediated through p53, the growth response of a p53 null cell line, H1299 lung carcinoma cells, was examined. The p53-null H1299 cells (Sanchez, Y. et al., *Science* 271:357–360 (1996)) was maintained in DMEM with 10% calf serum. Preconfluent cultures were given fresh medium supplemented with either 100 μM pTpT or diluent. Cells were collected on consecutive days by trypsinization, and counted by COULTER™ counter. As shown in FIG. 9, there was no inhibition of proliferation of pTpT-treated H1299 cells compared to diluent-treated controls.

The effect of pTpT on the level and intracellular distribution of p53 in normal neonatal fibroblasts was examined by immunoperoxidase staining using a p53-specific monoclonal antibody (mAb 421, Oncogene, Cambridge, Mass.). Preconfluent cultures were treated with either 100 μM pTpT or diluent for 24 hours before cell staining. Cells were first fixed for one minute in Histochoice fixative (Amresco, Solon, Ohio) followed by a five-minute rinse in PBS. p53 was detected using the Vectastain Elite ABC kit (Vector Laboratories, Burlingame, Calif.) and the p53-specific monoclonal antibody mAb 421. Within 24 hours, an increase in intranuclear p53 was detected in pTpT-treated cells compared to diluent-treated cells, as has been reported after UV-irradiation. These results are consistent with the induction of the p53-regulated genes GADD 45 and SDI 1 in fibroblasts as well as in SCC12F cells, by pTpT.

In another experiment, pTpT was found to induce the expression of SDI 1 mRNA in a p53-dependent manner. Preconfluent cultures of H1299 cells were transfected with an expression vector containing the wild type human p53 cDNA under the control of the human cytomegalovirus promoter/enhancer (Dr. Bert Vogelstein, Johns Hopkins Oncology Center). Control transfections were performed using the vector from which the p53 cDNA was removed. Transfections were carried out using the Lipofectin Reagent Kit (GIBCO/BRL). One day after transfection, cells were collected for Western blot analysis using 20 μg total protein as described (Yaar, M. et al., *J. Clin. Invest.* 94:1550–1562 (1994)). p53 was detected using mAb 421, anti mouse Ig linked to horseradish peroxidase (AMERSHAM, Arlington Heights, Ill.) and an ECL-kit (AMERSHAM) following the directions of the manufacturer. At the time of protein collection, duplicate cultures of H1299 cells transfected with the p53 expression vector (designated "p53") or control vector ("Ctrl") were given either diluent (DMEM) or 100 μM pTpT. After 24 hours, the cells were collected, processed for RNA isolation and Northern blot analysis with an SDI 1 cDNA probe. The autoradiograph was scanned using a Macintosh IIsi computer and Macintosh One Scanner, and the brightness and contrast were adjusted to display differences in autoradiographic signals maximally. The results indicated that p53-null H1299 cells express a very low level of the SDI 1 transcript and this level is not affected by addition of pTpT. Transfection of these cells with a wild-type p53 expression vector increased the level of SDI 1 and rendered this transcript inducible by addition of pTpT. Western analysis confirmed that H1299 cells normally express no p53 and that transfected H1299 cells expressed high levels of p53. These data indicate that pTpT increases the transcriptional activity of p53.

EXAMPLE 8

Enhancement of DNA Repair

Expression of a UV-damaged reporter plasmid containing the bacterial chloramphenicolacetyltransferase (CAT) gene under the control of SV40 promoter and enhancer sequences was previously shown to detect decreased DNA repair capacity in human lymphocytes associated with aging and early-onset skin cancers. This reporter plasmid was used to measure the DNA repair capacity of normal neonatal human skin-derived fibroblasts and keratinocytes.

Newborn keratinocytes were established as described (Stanulis-Praeger, B. M. and Gilchrest, B. A., *J. Cell. Physiol.* 139:116–124 (1989)) using a modification of the method of Rheinwald and Green (Gilchrest, B. A. et al., *J. Invest. Dermatol.* 101:666–672 (1993)). First-passage keratinocytes were maintained in a non-differentiating low $Ca^{2+}$ medium (K-Stim, Collaborative Biomedical Products, Bedford, Mass.). Fibroblasts were established from dermal explants as described (Rheinwald, J. G. and Green, J, *Cell* 6:331–343 (1975)) and maintained in DMEM supplemented with 10% bovine serum. Cells were treated with either 100 μM pTpT or an equal volume of diluent (DMEM) for five days prior to transfection. Duplicate cultures of each condition were transfected using the Lipofectin Reagent Kit (GIBCO/BRL) and 5 μg reporter DNA, pCAT-control vector (PROMEGA, Madison, Wis.). Before transfection, the vector DNA was either sham irradiated or exposed to 100 mJ/cm$^2$ UVB radiation from a 1 KW Xenon arc solar simulator (XMN 1000-21, Optical Radiation, Azuza, Calif.) metered at 285±5 nm using a research radiometer (model IL 1700A, International Light, Newburyport, Mass.), as described (Yaar, M. et al., *J Invest. Dermatol.* 85:70–74 (1985)). Cells were collected 24 hours after transfection in a lysis buffer provided in the CAT Enzyme Assay System (PROMEGA, Madison, Wis.) using a protocol provided by the manufacturer. CAT enzyme activity was determined using the liquid scintillation counting protocol and components of the assay system kit. Labeled chloramphenicol [50–60 mCI (1.85–2.22 GBq) mmol] was purchased from New England Nuclear (Boston, Mass.). Protein concentration in the cell extracts was determined by the method of Bradford (Anal. Biochem. 72:248 (1986)). CAT activity was expressed as c.p.m./100 µg protein and is represented as percent activity of cells transfected with sham-irradiated, non-damaged, plasmid.

Figure 10:
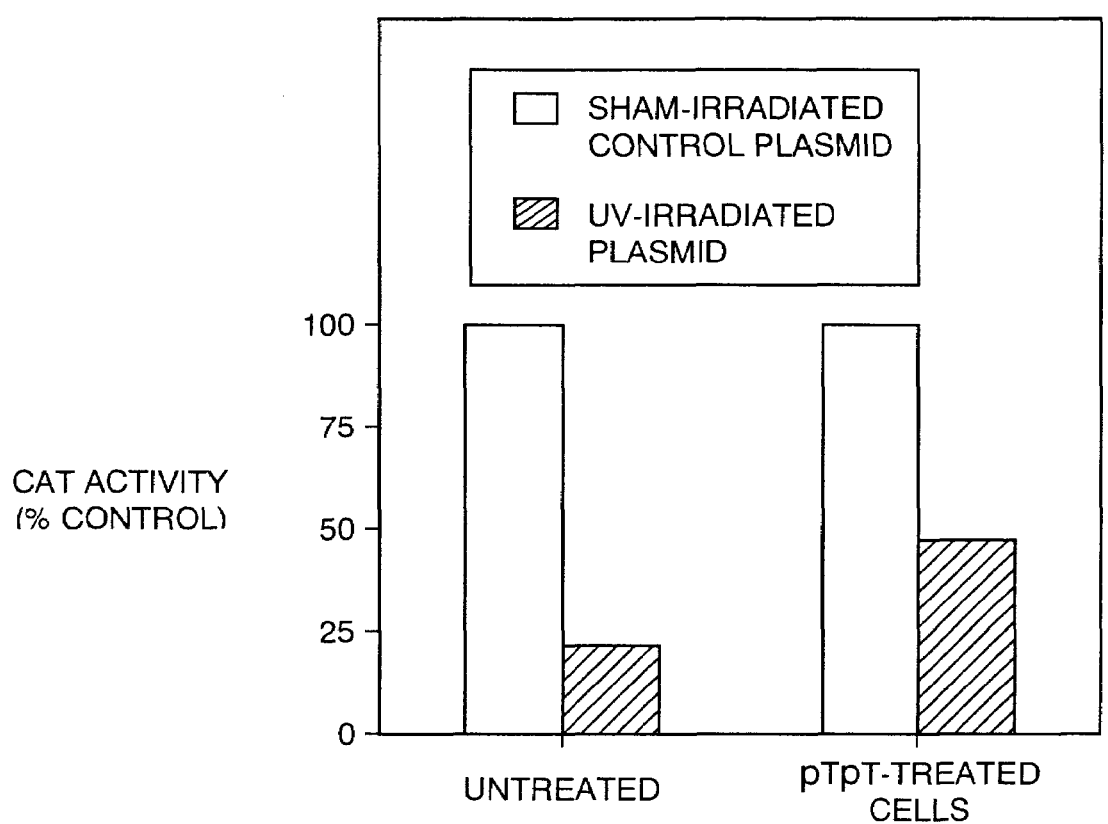
FIG. 10 is a graphic representation of enhancement of DNA repair of a reporter plasmid in human keratinocytes treated with pTpT, where open boxes represent sham-irradiated control plasmid and filled boxes represent UV-irradiated plasmid.
Figure 11:
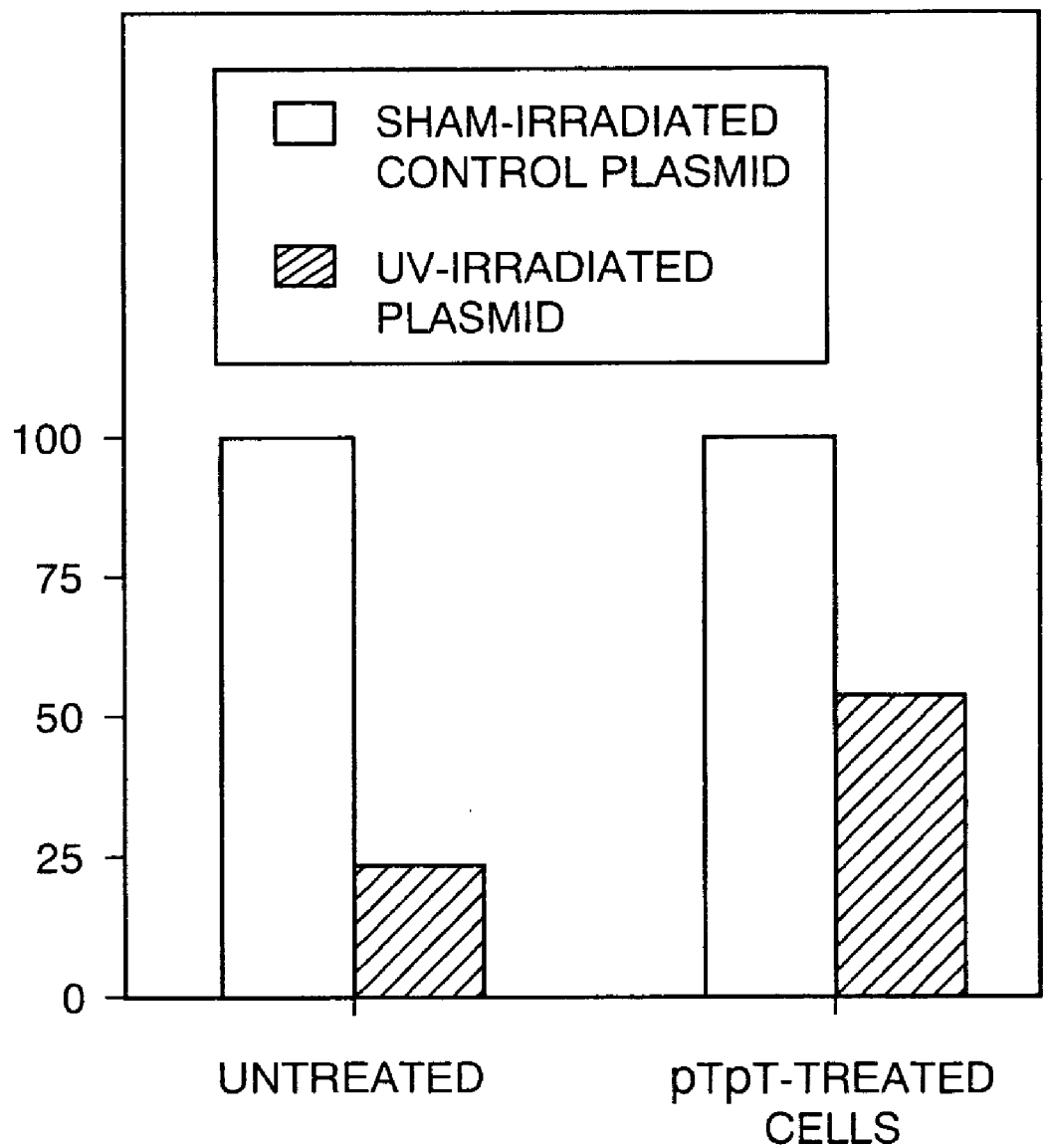
FIG. 11 is a graphic representation of enhancement of DNA repair of a reporter plasmid in human fibroblasts treated with pTpT where open boxes represent sham-irradiated control plasmid and filled boxes represent UV-irradiated plasmid.

In preliminary experiments, exposure of the plasmid to a dose of solar-simulated irradiation (100 mJ/cm$^2$, metered at 285 nm) prior to transfection was identified as resulting in approximately 75% reduction in CAT activity assayed in cell lysates 16–24 hours after transfection, compared to that of sham-irradiated plasmid transfected into paired cultures. However, keratinocytes (FIG. 10) and fibroblasts (FIG. 11) pretreated with 100 µM pTpT for five days before transfection displayed CAT activity more than 50% that of sham-irradiated transfected controls. Because the reporter plasmid was nonreplicating, the level of CAT activity directly reflects the degree of DNA repair of the UV-damaged CAT gene restoring its biological activity. These data indicate that pTpT treatment of normal human fibroblasts and keratinocytes more than doubles the capacity of cells to repair UV-induced DNA damage over a 24 hour period. The enhanced expression of UV-irradiated plasmid in pTpT-treated cells did not result from a general increase in plasmid transcription in these cells, because the expression of the sham-irradiated plasmid was not higher in non-pTpT-treated cells.

EXAMPLE 9

Activation of p53 and Repair of BP DNA Adducts

Cell Culture.

Newborn human keratinocytes were established using a modification (Stanislus et al. *J. Invest. Dermatol.* 90:749–754 (1998)) of the method of Rheinwald and Green (*Cell* 6:331–343 (1975)). First-passage keratinocytes were maintained in a non-differentiating medium containing a low concentration of calcium ion (K-Stim, Collaborative Biomedical Products, Bedford, Mass.).

The p53-null H1299 lung carcinoma cell line (AMERICAN TYPE CULTURE COLLECTION, ATCC, Rockville, Md.) was maintained in Dulbecco's modified Eagle's medium (DMEM;GIBCO/BRL, Gaithersburg, Md.) supplemented with 10% bovine serum (Hyclone Labs, Logan, Utah).

Transfection of H1299 Cells with a p53 Expression Vector.

Preconfluent cultures of H1299 cells were transfected with an expression vector containing the wild type human p53 cDNA under the control of the human cytomegalovirus promoter/enhancer (Dr. Bert Vogelstein, Johns Hopkins Oncology Center). Control transfections were performed using the same vector lacking the p53 cDNA. Transfections were carried out as described previously. One day after transfection, cells were collected for western blot using 20 µg total protein as described. p53 was detected using the monoclonal antibody DO-1 (Ab-6) known to detect both active and inactive forms of the protein (Oncogene, Cambridge, Mass.), anti-mouse Ig linked to horseradish peroxidase (AMERSHAM, Arlington Heights, Ill.) and an ECL-kit (AMERSHAM) following the direction of the manufacturer.

p53 Assay Using hGH Reporter Plasmid.

Normal human keratinocytes were transfected with the human growth hormone (hGH) reporter plasmid (pPG-GH) using the Lipofectamine Reagent Kit (GIBCO/BRL) as suggested by the manufacturer and 0.5 µg pPG-GH added to each p35 culture dish. pPG-GH contains the hGH coding region under the control of the thymidine kinase (TK) promoter and p53 consensus sequence, and hGH protein production is known to be proportional to p53 activity (Kern et al., 1992). Transfection was performed in the presence of 100 µM pTpT (Midland Certified Reagent Company, Midland, Tex.) or an equal volume of diluent. At the same time, the PSV β-galactosidase control vector (PROMEGA, Madison, Wis.) was co transfected to determine the transfection efficiency (Norton and Coffin, 1985). Four hours after transfection, medium was removed and replaced with K-Stim medium with or without 100 µM pTpT. Twenty-four hours after transfection and pTpT treatment, 400 µl of the medium was harvested from each 35 mm culture dish, and 100 µl of $^{125}$I-hGH antibody solution (Nichols Institute Diagnostics, San Juan Capistrano, Calif.) was added to detect secreted hGH as described below. The cells were harvested in a Reporter Lysis Buffer (PROMEGA) using a protocol provided by the manufacturer, and 150 µl of this lysate was used for the β-galactosidase assay using a β-galactosidase assay kit (PROMEGA). Samples from each of triplicate culture dishes were evaluated for hGH and β-galactosidase synthesis.

H1299 cells were similarly transfected with p53 expression vector or control vector. Two days after the transfection these cells were cotransfected with pPG-GH and PSV-β-galactosidase control vector, and treated with 100 µM pTpT. Twenty-four hours later, 250 µl of the medium and the cell lysate were harvested and processed as described above.

CAT Assay.

The pCAT vector (PROMEGA) was treated with benzo(a) pyrene-7,8-diol-9,10-epoxide (BPDE)—as described (Athas et al. *Cancer Res* 1991) to produce less damaged and more damaged plasmids, previously shown to be instructive in studies examining different repair capacities in human cells. Based on the incorporation of $^3$H-BPDE into the DNA, the less damaged plasmid contained 25 adducts per 5 kb plasmid and the more damaged plasmid contained 50 adducts. This non-replicating vector contains the chloramphenicol acetyltransferase gene under control of SV40 promoter and enhancer sequences. Human keratinocytes and p53-transfected H1299 cells were pre-treated with either 100 µM pTpT or an equal volume of diluent (DMEM) alone for 48 hours, then transfected with either BP-modified pCAT-control vector (0.5 µg/ml) or unmodified vector (0.5 µg/ml) together with PSV-pβ-galactosidase control vector (0.5 µg/ml). Cells were collected in a reporter lysis buffer (PROMEGA) 24 hours after transfection. CAT enzyme activity was determined using the liquid scintillation counting protocol and components of the assay system kit (PROMEGA). $^{14}$C-labeled chloramphenicol[50–60 mCi(1.85–2.22 GBq)mmol] was purchased from New England Nuclear (Boston, Mass.). CAT activity was normalized with β-galactosidase activity.

Western Blot Analysis.

Cells were treated with 100 μM pTpT or an equal volume of diluent alone for 48 hours. Total cellular proteins were collected in a buffer consisting of 0.25 M Tris HCl (pH 7.5), 0.375 M NaCl, 2.5% sodium deoxycholate, 1% Triton X-100, 25 mM $MgCl_2$, 1 mM phenylmethyl sulfonyl fluoride, and 0.1 mg ml aprotinin. Proteins (100 μg per sample) were separated by 7.5–15% SDS-PAGE and transferred to a nitrocellulose membrane (Schleicher & Schuell, Keene, N.H.). After transfer, the gel was stained with Coomassie Blue to verify even loading as visualized by the residual high molecular weight proteins. Membranes were blocked in 0.05% Tween-20/PBS with 5% milk, (Bio-Rad Laboratories, Hercules, Calif.). Antibody reactions were performed with the following antibodies: anti p53 (AB-6), anti PCNA (Ab-2) (Oncogene Science), and anti XPA (FL-273) (Santa Cruz Biotechnology). Sheep anti-mouse Ig linked to horseradish peroxidase (AMERSHAM, Arlington Heights, Ill.) (for p53 and PCNA) and goat anti-rabbit IgG (Bio-Rad)(for XP A) were used as the secondary antibodies. Binding was detected by the ECL detection kit (AMERSHAM).

To measure the repair of BP DNA adducts, non-replicating BP-damaged reporter plasmid system containing the bacterial chloramphenicol acetyltransferase (CAT) gene was used as described in Example 8. With first passage human keratinocytes, the transfection efficiency, as measured by the cotransfected β-galactosidase expression vector, was 40–70%. Compared to diluent-treated cells, pTpT-treated human keratinocytes showed an approximate doubling of CAT expression relative to paired cultures transfected with undamaged control CAT vector, when transfected with either the less BP-damaged (~25 adducts/plasmid) or the more BP-damaged (~50 adducts/plasmid) vector.

To confirm the activation of p53 by pTpT in a second assay, a reporter plasmid expressing the human growth hormone (hGH) gene under the influence of a p53 inducible promoter was employed. Activation of p53 increases its binding to the consensus sequence in the plasmid, leading to transcription of the hGH coding sequence and ultimately to secretion of hGH into the medium.

pTpT-treated human keratinocytes showed a 45%±25% increase in hGH secretion compared to diluent-treated cells. These data indicate that pTpT activates p53 in normal human keratinocytes as well as in p53-transfected H1299 cells.

To confirm that pTpT enhances repair of BP-DNA adducts through p53 activation, p53-null H1299 cells were transfected with the p53 expression vector, and p53 protein expression was then confirmed by western blot analysis 48 hours after transfection. In p53+H1299 cells, repair was comparable to that observed in normal keratinocytes; and the plasmid containing a low level of BP damage was repaired 80%±50% more efficiently in pTpT-pre-treated cells than in diluent pre-treated cells; and the plasmid containing a high level of BP damage was repaired more than three times as efficiently. In p53–H1299 cells, however, the repair capacity was the same as in both treatment groups. These data demonstrate that enhanced repair of BP-DNA adducts by pTpT requires p53.

pTpT activation of p53 in H1299 cells transiently transfected with the p53-responsive-hGH resulted in a 40% increase in hGH secretion compared to diluent-treated cells. These data further demonstrate that pTpT enhances p53 transcriptional activity through enhanced binding to its DNA consensus sequence.

Western blot analysis was used to examine the effect of pTpT treatment on the expression of selected genes known to be involved in DNA repair. Normal human keratinocytes were treated with pTpT for 2 days before harvesting cellular protein. pTpT up-regulated the levels of p53, PCNA and the XPA protein 2 to 3-fold within 2 days of treatment.

EXAMPLE 10

Immunosuppression and Inhibition of Contact Hypersensitivity in a Murine Model

C57B16 mice were subjected to the following treatment prior to sensitization with the allergen DNFB, by topical administration to abdominal skin; no pretreatment, UVB irradiation (200 $J/m^2$/dx4d), pTpT, pApA, or vehicle alone (30 μl of 100 μM BIDx5d). Mice pretreated with UVB or pTpT showed markedly suppressed ear swelling responses to DNFB challenge (0.6±0.2 and 0.9±0.3) compared to untreated or vehicle treated animals (4.3±0.6 and 3.3±0.2), whereas pApA-treated mice exhibited intermediate responses (2.5±0.6).

The immunomoduatory effect of pTpT was tested in vitro using human keratinocytes. Duplicate cultures of primary human keratinocytes were treated with pTpT, diluent or UVB irradiation (200 $J/m^2$) or sham irradiation. Cells were collected at various times after treatment and analyzed for IL-10 protein by ELISA and for IL-10 mRNA by RT-PCR. An increase in IL-10 mRNA was detected after 6 hours in irradiated cells and after 48 hours in pTpT treated cells. An increase in IL-10 protein of 18 pg/ml was detected 24 hours after irradiation and 15±2 pg/ml 72 hours after treatment with pTpT. Previous work has demonstrated functional inhibition of the allogenic mixed lymphocyte reaction (MLR) assay by IL-10. In the allogenic MLR, T cell activation is measured as lymphocyte proliferation, measured by $^3$H-thymidine incorporation. IL-10 activity of culture medium from the 72 hour pTpT sample was measured by addition of the >10 kD components (containing the 18 kD IL-10 protein). Reduction in T cell proliferation by 80±5% was demonstrated, compared to 8%±3 inhibition from diluent-treated control cultures. Thus, like UVB irradiation, pTpT induces IL-10 in human keratinocytes which is likely to cooperate with TNFα to inhibit contact hypersensitivity in pTpT treated skin.

In another experiment, TNFα gene activation was measured by utilizing mice carrying a CAT reporter transgene bearing the entire TNFα promoter and 3'-untranslated region. Transgenic mice were subjected to the following treatment prior to skin assay for CAT expression: UVB irradiation (200–700 $J/m^2$), intracutaneous injection of pTpT (100 μM); lipopolysaccharide (LPS 1 μg/ml) as positive control, or vehicle alone. CAT activity was detected in skin treated with UVB, LPS, or pTpT (but not with vehicle alone).

EXAMPLE 11

Oligonucleotide Dependent UV-mimetic Activity: Melanogenesis and p21/Waf1/Cip1 Expression The induction of melanogenesis in Cloudman S91 mouse melanoma cells by a five-nucleotide oligomer, CATAC, SEQ ID NO: 6 and a nine-nucleotide oligomer, GAGTATGAG (SEQ ID NO: 1) was examined. Duplicates of Cloudman S91 murine melanoma cells were incubated with either 100 μM oligo or an equal volume of diluent ($H_2O$) for 5 days. The cells were then collected, counted, and an equal number of cells were pelleted for melanin analysis. In three experiments, the pigment content after incubation with the 9-mer, 5-mer and pTpT increased 418%±267%, 61%±60% and 155%±60% of control levels, respectively. The 9-mer, but not the 5-mer, also stimulated melanogenesis in human melanocytes, producing a 51–62% increase after one week in culture. Variations of this oligonucleotide were evaluated: a scrambled 9-mer (TAGGAGGAT; SEQ ID NO: 2) and two truncated versions, a 7-mer (AGTATGA; SEQ ID NO: 3) and second 5-mer (GTATG; SEQ ID NO: 4). Both 9-mers were equally active, inducing a 800% increase in melanin content. The truncated versions (SEQ ID NOs: 3 and 4) were also active, inducing 640% and 670% increases, respectively. As with pTpT, SEQ ID NO: 1 (9-mer) oligonucleotide, but not SEQ ID NO: 6 (5-mer) induced the expression of the p21/Waf 1/Cip 1 gene within 48 hours in a squamous cell carcinoma line, increasing the level of this mRNA 200–300%, compared to a 100–150% increase from pTpT.

Together, these data show that the UV-mimetic activity of pTpT can be duplicated quite dramatically by other oligonucleotides.

EXAMPLE 12

Melanogenesis

Figure 12:
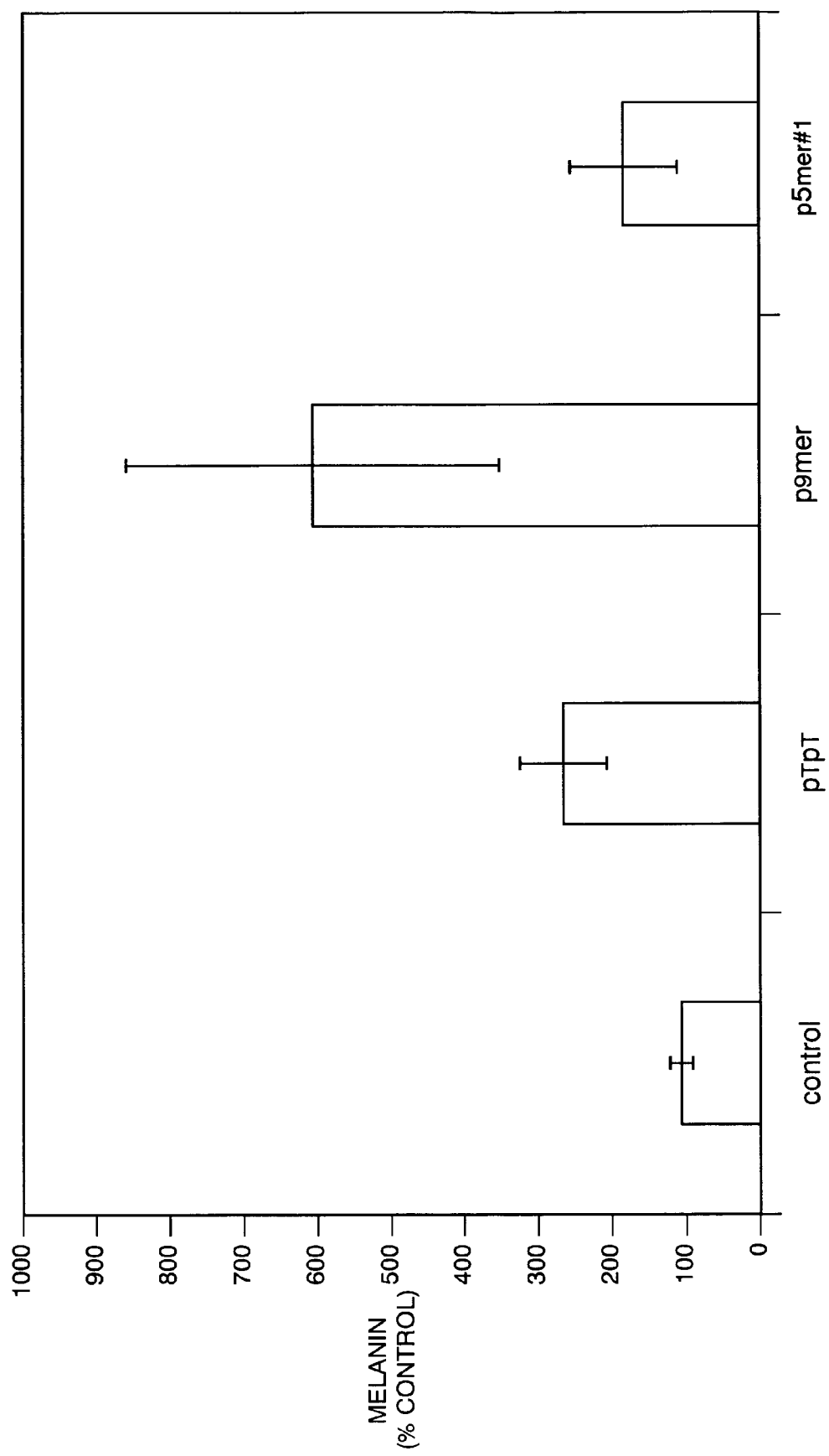
FIG. 12 is melanin content of Cloudman S91 cells treated with 100 μM of the indicated oligonucleotide or an equal volume of diluent for 5 days, where data are shown as averages of duplicate cultures calculated as a percentage of diluent-treated controls.

Cultures of Cloudman S91 murine melanoma cells were treated for 5 days with SEQ ID NO: 1, SEQ ID NO: 6, pTpT as a positive control, or an equal volume of diluent as a negative control. Spectrophotometric analysis of S91 cell pellets after oligonucleotide treatment showed the melanin content of pTpT-treated cells to be 255+/−60% that of control cells (FIG. 12). SEQ ID NO: 6 produced a slight increase in melanin, to 165+/−77% of control levels. SEQ ID NO: 1 stimulated melanin content to an average of 600+/−260% of control levels.

Figure 17:
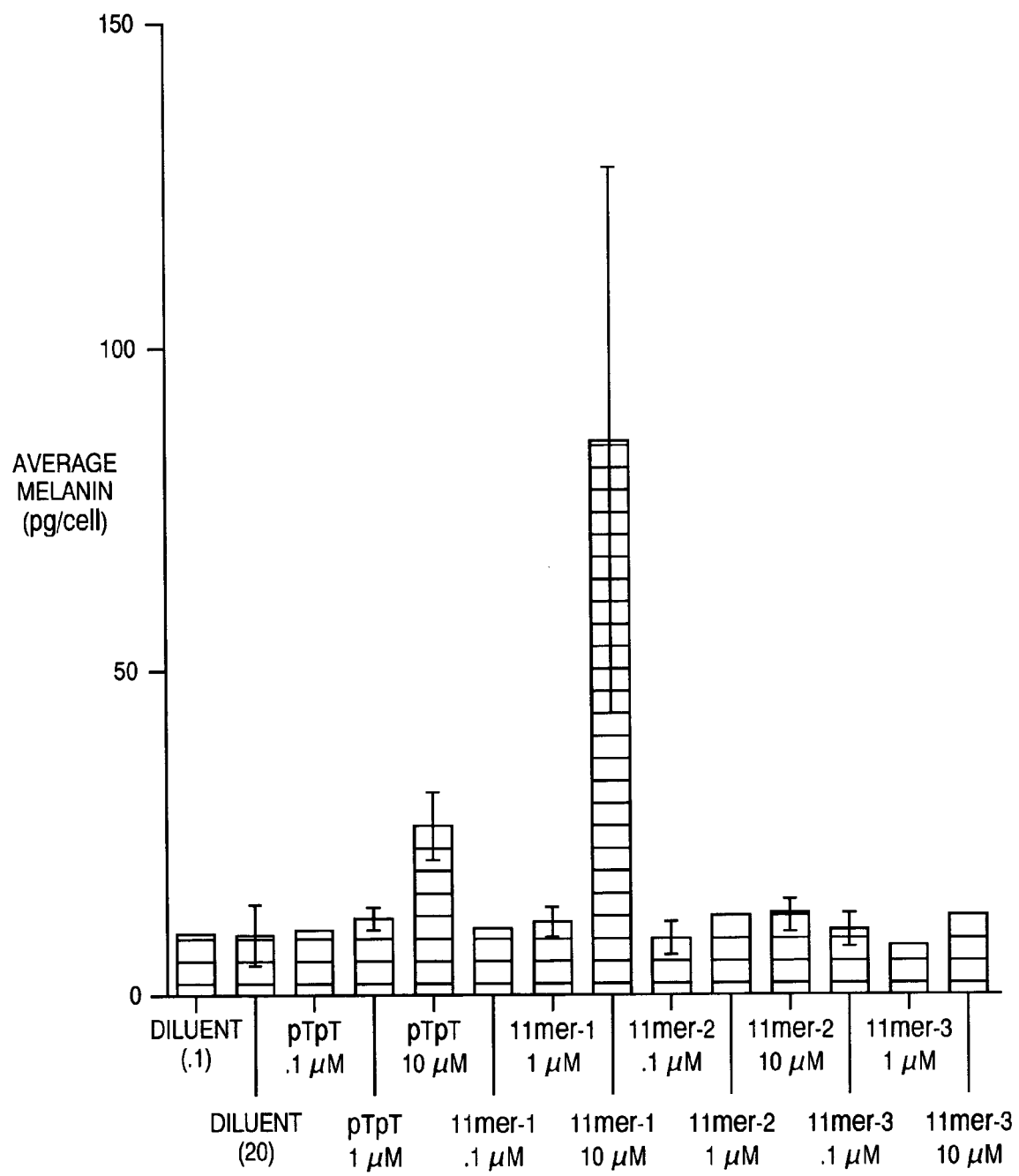
FIG. 17 shows melanin content of Cloudman S91 cells treated with the indicated oligonucleotide.
Figure 18:
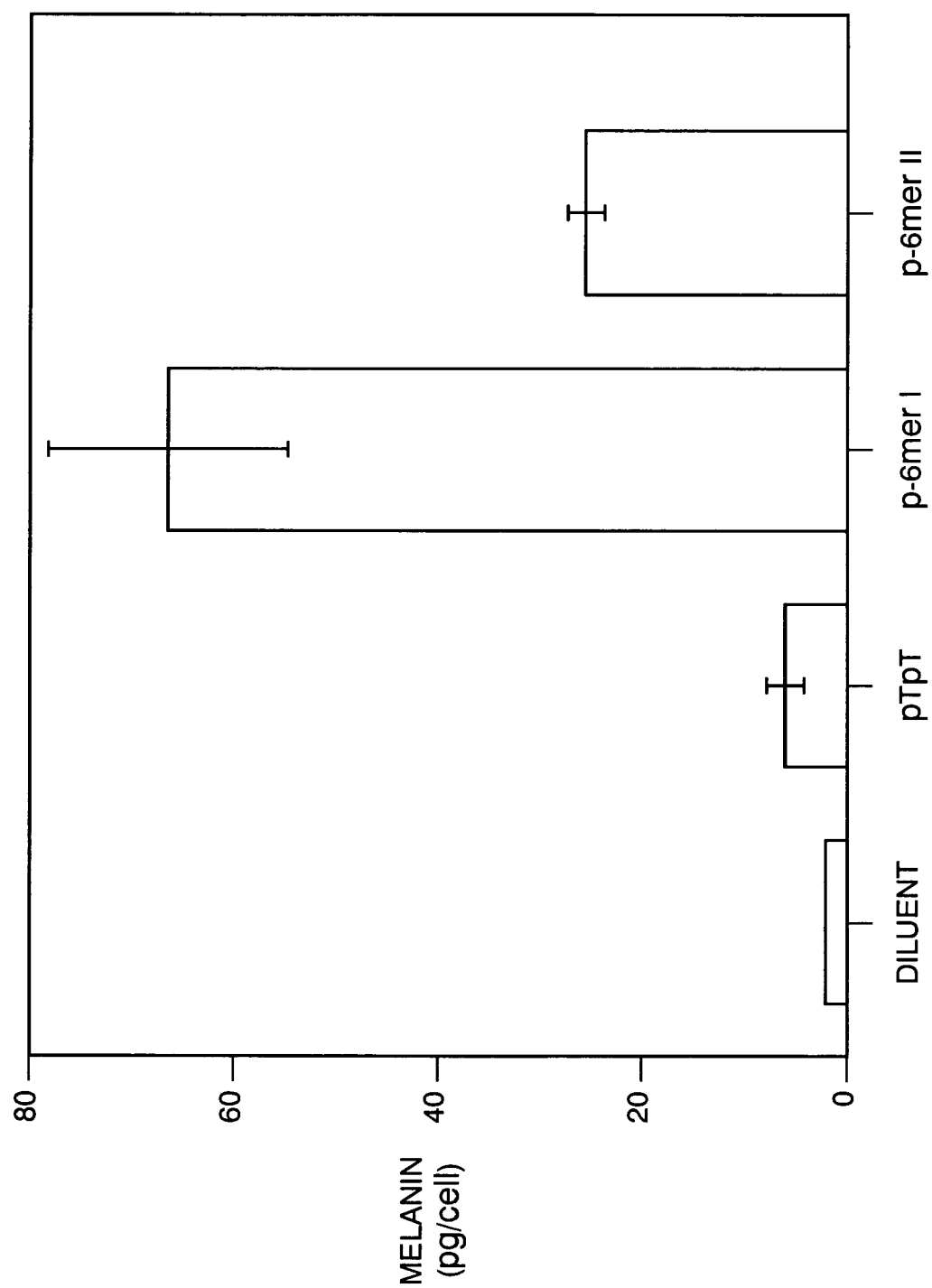
FIG. 18 shows melanin content of Cloudman S91 cells treated with the indicated oligonucleotide.

Oligonucleotides GTTAGGGTTAG (SEQ ID NO: 5), CTAACCCTAAC (SEQ ID NO: 9), or GATCGATCGAT (SEQ ID NO 10), each comprising a 5' phosphate were added to cultures of Cloudman S91 melanoma cells as described in Example 11.

pTpT, shown previously to stimulate pigmentation in these cells, was used as a reference treatment and diluent alone as a negative control. After five days of treatment with the oligonucleotides, the cells were collected, counted, and an equal number of cells were pelleted for melanin analysis. The data shown in FIG. 17 demonstrate that 10 µM pTpT increased melanin content to 3 times that of control diluent-treated cells. SEQ ID NO: 5, representing the telomere over-hang sequence, also at 10 µM, increased the melanin level to 10 times that of control cells. SEQ ID NO: 9 (telomere over-hang complement) and SEQ ID NO: 10 (unrelated sequence) did not produce significant change in pigment content at concentration up to 10 µM. A truncated version of SEQ ID NO: 5, comprising TTAGGG (SEQ ID NO: 11) was also highly melanogenic, while the reverse complimentary sequence CCCTAA (SEQ ID NO:12) was less active (FIG. 18), where both oligonucleotides contained a 5' phosphate).

The compounds of the present invention were tested for skin penetration and in vivo melanogenic activity. Mice were treated (on their ears) with fluorescently-labeled pTpT or SEQ ID NO: 1 (comprising a 5' phosphate) in propylene glycol for 4 hours, then were sectioned and examined by confocal microscopy. Treatment with either oligonucleotide resulted in brightly stained epidermis and hair follicles. Thus pTpT and SEQ ID NO: 1 comparably penetrate the skin barrier.

Figure 13:
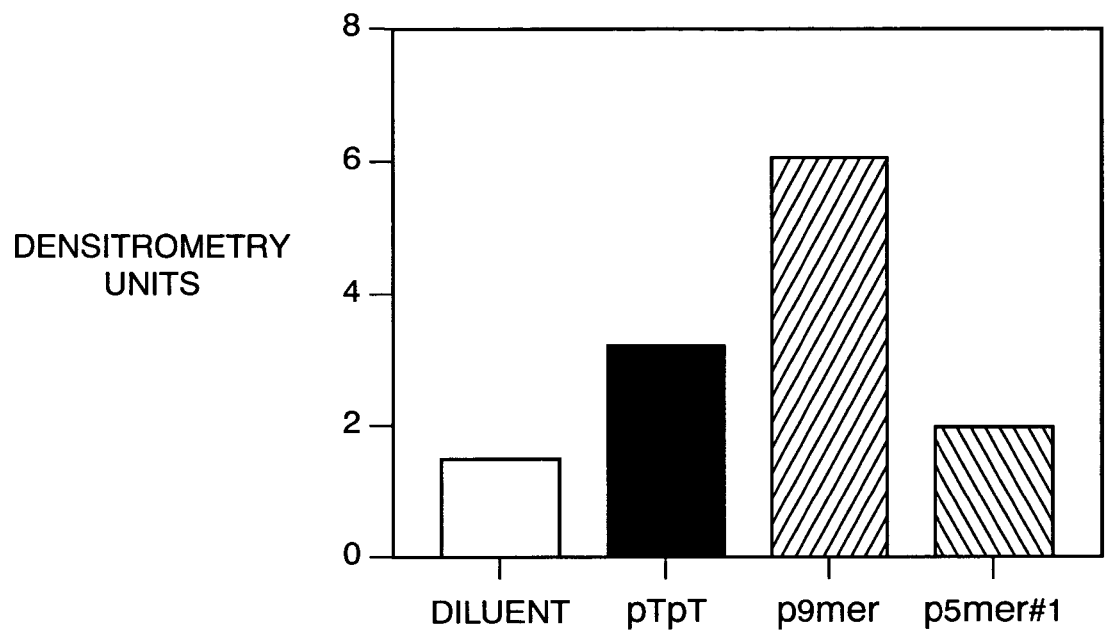
FIG. 13 shows a densitometric analysis of p21 expression detected by Northern blot analysis of SCC12F cells treated with 100 μM of the indicated oligonucleotide or an equal volume of diluent for 48 hours.
Figure 14:
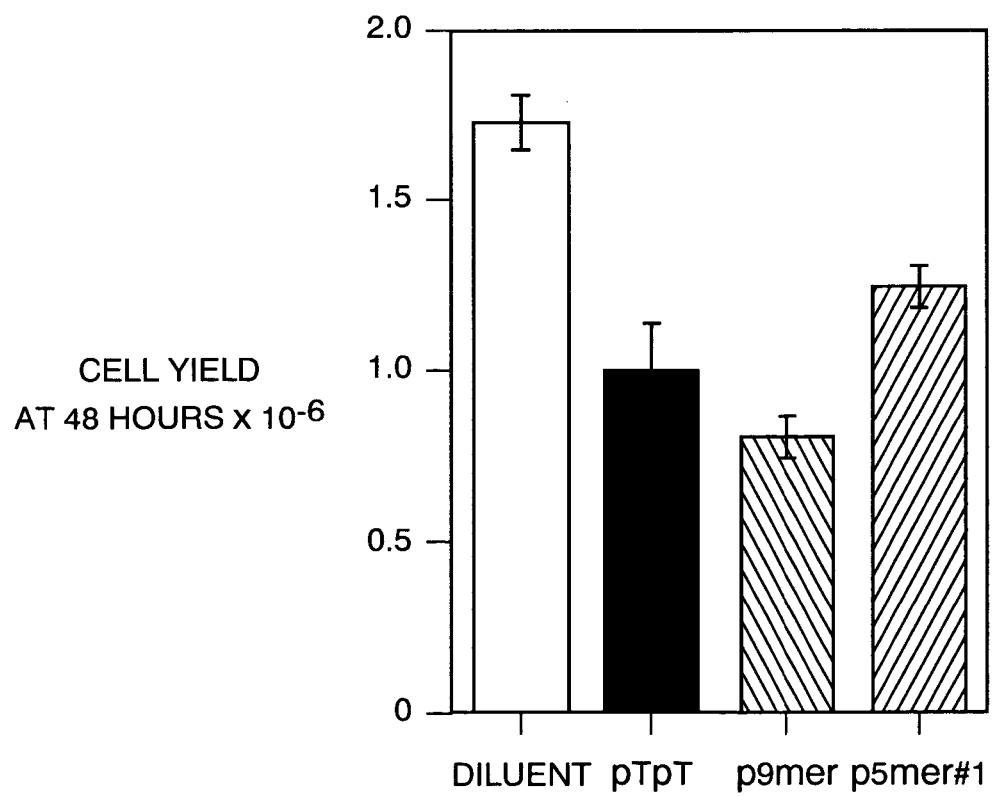
FIG. 14 shows cell yields of the samples in FIG. 13, as mean±standard deviation.

In another experiment, mice were treated once daily with either 100 µM pTpT or SEQ ID NO: 1 containing a 5' phosphate in propylene glycol on one ear, or vehicle alone on the other ear. After 15 days, when the ears were sectioned and stained with Fontana Masson to detect melanin compared to vehicle controls, there was a 70% increase in pigmentation in pTpT-treated ears and a 250% increase with SEQ ID NO: 1. Thus, both compounds comprising as few as 2 and as many as 9 nucleotides are effective at producing the in vitro UV-mimetic effects in vivo.

p53 Activation and Cell Proliferation pTpT was previously found to inhibit cell cycle progression, at least in part through activation of p53 and subsequent upregulation of the cyclin dependent kinase inhibitor p21. Cultures of the human keratinocyte line SCC12F were treated with pTpT, SEQ ID NO: 1, SEQ ID NO: 6 or diluent alone as a negative control, collected and counted 48 hours later and processed for northern blot analysis of p21 mRNA expression. SEQ ID NO: 1 was found to increase the level of p21 mRNA to almost 3-fold that of diluent control levels while pTpT-treated cells showed p21 mRNA levels twice that of control cells (FIG. 13). Cells treated with SEQ ID NO: 6 showed a 10–20% increase in p21 mRNA level. In these paired dishes, SEQ ID NO: 1 also reduced cell number by approximately 50% after 2 days, while pTpT and SEQ ID NO: 6 caused 40% and 25% reductions, respectively (FIG. 14). Thus, the sequences of the present invention activate p53 and inhibit cell proliferation similar to the effect of pTpT.

Effect of Size and Sequence

Figure 15:
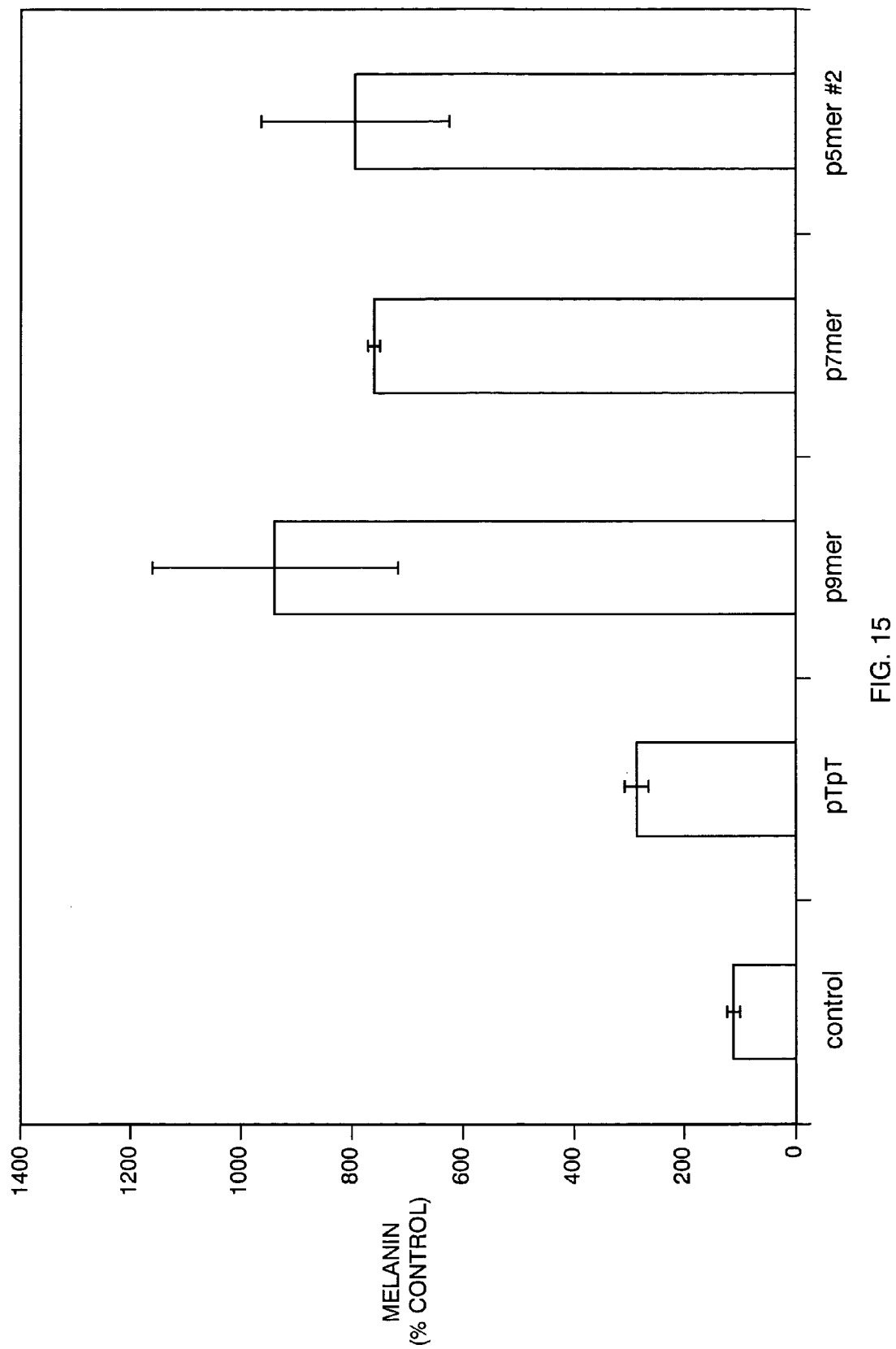
FIG. 15 shows melanin content of Cloudman S91 cells treated with 100 μM of the indicated oligonucleotide or an equal volume of diluent for 5 days as a percent of diluent-treated controls (mean±standard deviation) for 3 independent experiments.

S91 cells were cultured in the presence of either pTpT SEQ ID NOS: 1, 7, 4 or diluent alone. After 5 days, the cells were collected, counted and an equal number of cells were pelleted for melanin analysis (FIG. 15). pTpT produced a moderate increase in melanin content and SEQ ID NO: 1, a larger increase. In addition, SEQ ID NOS: 4 and 7 also strongly stimulated melanogenesis. Both SEQ ID NOS: 4 and 7 stimulated a 7–8 fold increase in melanin. Because one p5mer was much more effective at inducing melanin production (compare results for SEQ ID NO: 4 and 6), these data suggest that oligonucleotide sequence plays a role in determining its melanogenic activity.

Figure 16:
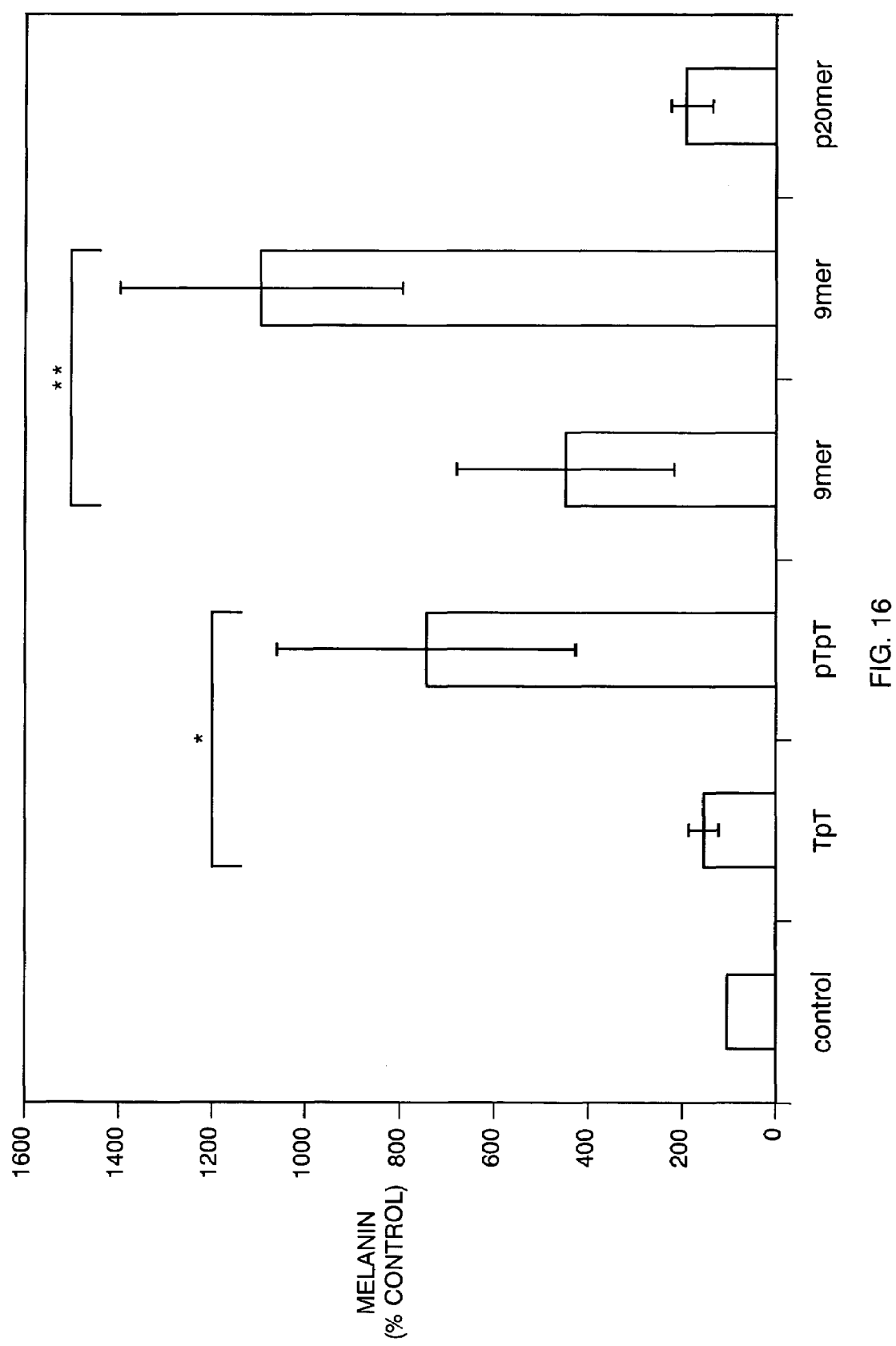
FIG. 16 shows melanin content of Cloudman S91 cells treated with 100 μM of the indicated oligonucleotide or an equal volume of diluent as described for FIG. 12, where the values represent three independent experiments and where *=p<0.004, **=p<0.03, two-tailed student's t-test.

A p20mer was synthesized (SEQ ID NO: 8), with 3 repeats of the 4-base sequence GCAT, followed by two repeats TACG, an oligonucleotide with an internal pTpT that resembles the 27–29 base fragment excised during excision repair of thymine dimers in eukaryotic cells. This oligonucleotide stimulated pigmentation to twice the level of control cells (FIG. 16).

Effect of 5' Phosphorylation

S91 cells were cultured for 5 days in the presence of the thymidine dinucleotides or SEQ ID NO: 1 with or without a 5' phosphate or diluent alone as a negative control. Removal of the 5' phosphate significantly reduced the melanogenic activity of pTpT by 80% and of the 9mer by 60% (p<0.04 and p<0.03, respectively, two-tailed students' T-test, FIG. 16. These data are consistent with an intracellular site of action of these oligonucleotides and with the reported requirement of a 5' phosphate for efficient cellular uptake.

5' Phosphorylation Increases Oligonucleotide Uptake.

Fluorescein phosphoramidite (FAM) labeled oligonucleotides were added to cultures of S91 cells for 4 hours and the cells were then prepared for confocal microscopy. Nuclei, identified by staining with propidium iodide, appeared red and FAM-labeled oligonucleotides appeared green. Co-localization of red and green signals was assigned a yellow color by the computer. Oligonucleotides with a 5' phosphate showed greater cellular uptake than those lacking this moiety. Confocal microscopy failed to detect uptake of TpT and fluorescence-activated cell sorting (FACS) analysis of these cells and gave a profile similar to that seen with untreated cells. pTpT-treated cells showed strong green fluorescence in the cytoplasm, but only a small amount of nuclear localization. FACS analysis showed a shift in the peak fluorescence intensity, compared to TpT-treated cells, indicating more intensely stained cells. Similarly, the presence of the phosphate at the 5' end of SEQ ID NO: 1 greatly enhanced its uptake into the S91 cells. SEQ ID NO: 1 without 5' phosphorylation showed only moderate uptake and was localized predominantly in the cytoplasm, with faint nuclear staining in only some cells, whereas SEQ ID NO: 1 with 5' phosphorylation showed intense staining that strongly localized to the nucleus. FACS analysis of SEQ ID NO: 1 without 5' phosphorylation showed a broad range of staining intensities with essentially two populations of cells, consistent with the confocal images. The phosphorylated SEQ ID NO: 1 containing cells also showed a range of staining intensities, but with more cells showing higher fluorescent intensity. Cells treated with phosphorylated SEQ ID NO: 8 showed a pattern of fluorescence very similar to that seen with phosphorylated SEQ ID NO: 1, both by confocal microscopy and FACS analysis, indicating that its lower activity in the melanogenesis assay cannot be ascribed to poor uptake. These data show that uptake of these oligonucleotides by S91 cells is greatly facilitated by the presence of 5' phosphate and that melanogenic activity, while consistent with a nuclear site of action, is not solely dependent on nuclear localization. Also, although the total intracellular fluorescence did not increase appreciably with increasing oligonucleotide length among the DNAs tested, the larger oligonucleotides more readily accumulated in the cell nucleus. There was no change in the profile of oligonucleotide uptake after 6 and 24 hours.

EXAMPLE 13

Figure 19:
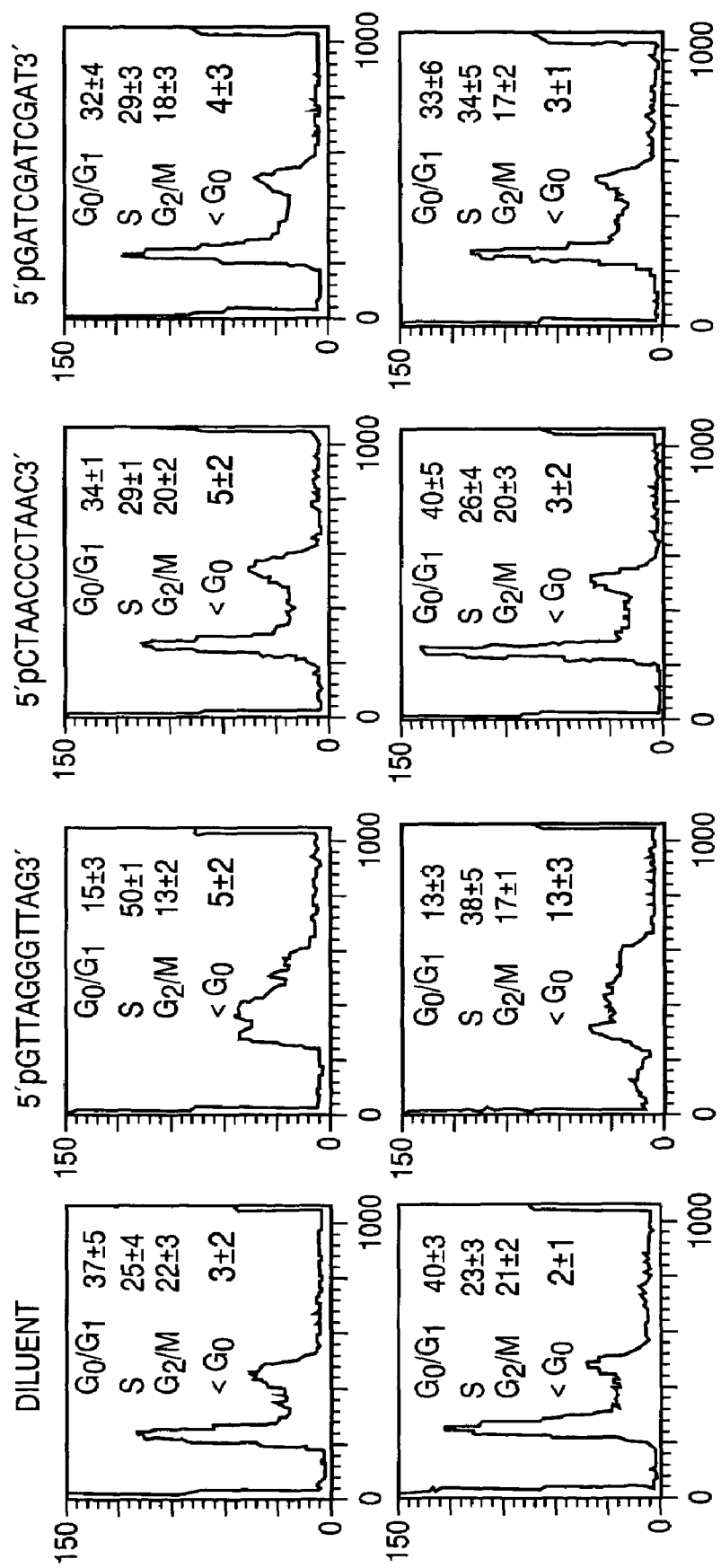
FIG. 19 shows FACS analysis of propidium iodide stained cells, treated with 40 μM of the indicated oligonucleotide.

Oligonucleotides homologous to the telomere overhang repeat sequence (TAAGGG) sequence (11mer-1: SEQ ID NO: 5), complementary to this sequence (11mer-2: SEQ ID NO: 9) and unrelated to the telomere sequence (11mer-3: SEQ ID NO: 10) were tested. The three 11-mer oligonucleotides were added to cultures of Jurkat cells, a line of human T cells, one of the cell types reported to undergo apoptosis in response to telomere disruption. Within 48 hours, 50% of the cells treated with 40 µM of SEQ ID NO:5 had accumulated in the S phase, compared to 25–30% for control cells ($p<0.0003$, non-paired t-test), and by 72 hours, 13% of these cells were apoptotic as determined by a sub-$G_0/G_1$ DNA content, compared to 2–3% of controls ($p<0.007$, non-paired t-test) (FIG. 19). At 96 hours, 20±3% of the 11mer-1 treated cells were apoptotic compared with 3–5% of controls ($p<0.0001$, non-paired t-test). To exclude preferential uptake of the 11mer-1 as an explanation of its singular effects, Jurkat cells were treated with oligonucleotides labelled on the 3' end with fluorescein phosphoramidite, then subjected to confocal microscopy and FACS analysis. The fluorescence intensity of the cells was the same after all treatments at 4 hours and 24 hours. Western analysis showed an increase in p53 by 24 hours after addition of 11mer-1, but not 11mer-2 or -3, with a concomitant increase in the level of the E2F1 transcription factor, known to cooperate with p53 in induction of apoptosis and to induce a senescent phenotype in human fibroblasts in a p53-dependent manner as well as to regulate an S phase checkpoint.

EXAMPLE 14

The Effect of DNA Fragments on DNA Mutation Frequency In Vivo

Transgenic mice carrying multiple genomic copies of a LacZ reporter plasmid were used. One hundred µM pTpT in polypropyleneglycol was applied to one ear and vehicle alone to the other ear, daily for four days. On the fifth day, both ears were exposed to 100 mJ/cm$^2$ UVB light. This procedure was repeated weekly for 3, 5 or 7 weeks (3 mice/group). One week after the final irradiation, LacZ plasmids were harvested from the ear epidermis. Using methods well known in the art, the plasmids were recovered from genomic DNA by restriction enzyme digestion and specific binding to the lack LacI protein. Mutant LacZ plasmids were positively selected by transfection into bacteria and growth on selective medium and the mutation frequency was determined. After 3, 5, 7 weeks, pTpT-treated skin exhibited a 20–30% lower mutation frequency than diluent treated skin (200 vs 293, 155 vs 216, and 261 vs 322, respectively). These data showed that pTpT-enhanced DNA repair reduces UV-induced mutations in vivo and suggest that topical application could be used to lower the mutation rate in carcinogen-exposed human skin.

EXAMPLE 15

Oxidative Damage

Primary newborn fibroblasts were treated for 3 days with 10 µM pTpT or diluent as control and then treated with $5\times10^{-5}$ or $5\times10^{-4}$ M $H_2O_2$. Within 72 hours of $H_2O_2$ exposure, cell yields of pTpT pre-treated cultures were 45±1% and 739±5% higher, respectively, compared to diluent pre-treated control samples. 72 hours after exposure of the low $H_2O_2$ dose, only 9.6±2.4% of the diluent pre-treated cells survived. In contrast, pTpT pre-treatment increased cell survival by 2–9 fold at $5\times10^{-4}$ M $H_2O_2$ and conferred complete protection at the low dose. mRNA levels of Cu/Zn superoxide dismutase, an enzyme that participates in the process of oxygen radical quenching, were increased by greater than 3 fold 48 and 72 hours after pTpT treatment and remained elevated at least 24 hours after pTpT withdrawal (when the experiment was terminated).

EXAMPLE 16

Age Related Decline in DNA Repair Capacity

Human dermal fibroblasts (fb), derived from newborn, young adult (25–35 y), and older adult (65–90 y) donors were pre-treated with 10 µM pTpT or SEQ ID NO: 1 containing a 5' phosphate or diluent as a control for 24 hours. The samples were then UV irradiated with 5, 10 and 30 m/cm$^2$. DNA and proteins were collected at time 0 and up to 24 hours post-UV. As previously reported, there were age-associated decreases in the constitutive and UV-induced protein levels of p53, p21, XPA, RPA ERCC/PF and PCNA. However, in all age groups, pre-treatment with oligonucleotides resulted in up-regulated constitutive and UV-induced levels of these proteins by 200–400%. Furthermore, slot blot analysis specific for thymine dimers and (6–4) photoproducts showed a significant decrease with aging in the DNA repair states in the first 16 hours post-UV. Pre-treatment with oligonucleotides increased the removal of photoproducts by 30–60 percent.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of reducing photoaging in a mammal, comprising administering to the epidermis of the mammal a composition comprising an effective amount of at least one DNA oligonucleotide, wherein said oligonucleotide is approximately 2–200 nucleotides in length, and wherein the oligonucleotide comprises a phosphodiester backbone.

2. The method of claim 1, wherein said oligonucleotide consists of a nucleotide sequence or a portion of a sequence selected from the group consisting of SEQ ID NOs: 1, 2, 3, 4, 5, 6, 8 and 11.

3. The method of claim 1, wherein said oligonucleotide is single-stranded.

4. The method of claim 1, wherein the oligonucleotide comprises a 5' phosphate.

5. The method of claim 1, wherein said oligonucleotide is at a concentration of about 1 μM to about 500 μM.

6. The method of claim 1, wherein the oligonucleotide comprises a physiologically acceptable carrier.

7. A method of increasing melanin production in epidermal melanocytes of a mammal, said method comprising topically administering to said epidermal melanocytes an effective amount of a composition comprising at least one oligonucleotide, wherein the oligonucleotide has a phosphodiester backbone, and wherein the oligonucleotide has a nucleotide sequence consisting of SEQ ID NO:5, SEQ ID NO:3, or SEQ ID NO: 11.

8. The method of claim 7, wherein said oligonucleotide has a nucleotide sequence consisting of SEQ ID NO: 5 or a portion thereof.

9. The method of claim 7, wherein the oligonucleotide is single-stranded.

10. The method of claim 7, wherein the oligonucleotide comprises a 5' phosphate.

11. The method of claim 7, wherein the oligonucleotide is at a concentration of about 1 μM to about 500 μM.

12. The method of claim 7, wherein the composition comprises a physiologically acceptable carrier.

13. A method of increasing melanin production in epidermal melanocytes of a mammal, comprising topically administering the epidermal melanocytes an effective amount of at least one oligonucleotide having a phosphodiester backbone, wherein the oligonucleotide consists of at least one sequence selected from the group consisting of: pTpT, SEQ ID NO: 1, SEQ ID NO:3, SEQ ID NO:5, and SEQ ID NO:11.

14. The method of claim 13, wherein the oligonucleotide is single-stranded.

15. The method of claim 13, wherein the oligonucleotide comprises a 5' phosphate.

16. The method of claim 13, wherein the oligonucleotide is at a concentration of about 1 μM to about 500 μM.

17. The method of claim 13, wherein the composition comprises a physiologically acceptable carrier.

18. A method of increasing DNA repair in epithelial cells, comprising applying directly to said cells an effective amount of a composition consisting of pTpT.

19. The method of claim 18, wherein the pTpT is at a concentration of about 1 μM to about 500 μM.

20. The method of claim 18, wherein the composition comprises a physiologically acceptable carrier.

21. A method of inhibiting proliferation of epithelial cells, comprising topically administering to said cells an effective amount of a composition consisting pTpT.

22. The method of claim 21, wherein the pTpT is at a concentration of about 1 μM to about 500 μM.

23. The method of claim 21, wherein the composition comprises a physiologically acceptable carrier.

24. A composition comprising at least one oligonucleotide, said oligonucleotide having a phosphodiester backbone, and a physiologically acceptable carrier, wherein the sequence of said oligonucleotide consists of SEQ ID NO: 5 and wherein said composition is suitable for medicinal or cosmetic use.

25. The composition of claim 24, wherein at least one said oligonucleotide comprises a 5' phosphate.

26. A composition comprising at least one oligonucleotide, said oligonucleotide comprising a phosphodiester backbone, and a physiologically acceptable carrier, wherein the sequence of said oligonucleotide consists of SEQ ID NO:3 and wherein said composition is suitable for medicinal or cosmetic use.

27. The composition of claim 26, wherein at least one said oligonucleotide comprises a 5' phosphate.

28. A composition comprising at least one oligonucleotide, said oligonucleotide comprising a phosphodiester backbone, and a physiologically acceptable carrier, wherein the sequence of said oligonucleotide consists of SEQ ID NO: 1, SEQ ID NO: 2, SEQ ID NO: 3 or SEQ ID NO: 4, and wherein at least one said oligonucleotide comprises a 5' phosphate, and wherein said composition is suitable for medicinal or cosmetic use.

29. A method of increasing p53 activity in epidermal cells of a mammal, said method comprising topically administering an effective amount of $d(pT)_2$, or an oligonucleotide having a nucleotide sequence consisting of SEQ ID NO: 1 or SEQ ID NO:6 to said cells.

30. The method of claim 29 wherein activation of p53 results in nucleotide excision repair in the cell.

31. A method of treating hyperproliferative disease affecting epithelial cells in a mammal, comprising directly administering to the epithelial cells an effective amount of a composition comprising at least one DNA oligonucleotide comprising a phosphodiester backbone, wherein the oligonucleotide has a nucleotide sequence consisting of SEQ ID NO: 1, SEQ ID NO:6 or pTpT.

32. The method of claim 31, wherein pTpT is ultraviolet-irradiated.

33. The method of claim 31, wherein an effective amount of said composition is administered in a delivery vehicle.

34. The method of claim 33, wherein the delivery vehicle comprises liposomes.

35. The method of claim 33, wherein the delivery vehicle comprises propylene glycol.

36. The method of claim 31, wherein an effective amount of said composition is administered by aerosol.

37. The method of claim 31, wherein the mammal is a human.

38. The method of claim 31, wherein the epithelial cells are carcinoma cells.

39. A method of inhibiting proliferation of skin cells in a mammal, comprising administering topically to the skin cells an effective amount of a composition comprising DNA fragments that are approximately 2–200 nucleotides in length, the DNA fragments being selected from the group consisting of, DNA dinucleotides, DNA dinucleotide dimers and any of the foregoing combinations thereof.

40. A method of inhibiting or reducing DNA damage in epidermal cells of a mammal, wherein said DNA damage is caused by UV irradiation, said method comprising topically administering to the cells in the mammal an effective amount of a composition comprising DNA fragments that are approximately 2–200 nucleotides in length, the DNA fragments being selected from the group consisting of: single-stranded DNA fragments, deoxynucleotides, dinucleotides, dinucleotide dimers and combinations thereof.

41. A method of inhibiting growth of malignant cells in a mammal, comprising directly administering to said cells an effective amount of DNA fragments that comprise a phosphodiester backbone and are about 2–200 nucleotides in length, the DNA fragments being selected from the group consisting of: single-stranded DNA fragments, DNA dinucleotides, DNA dinucleotide dimers and a combination of any of the foregoing.

42. The method of claim 39, wherein said skin cells are selected from the group consisting of: epithelial cells, melanocytes, keratinocytes and fibroblasts.

43. A method of increasing melanin production in epidermal cells of a mammal, said method comprising topically administering to said cells an effective amount of a composition comprising at least one single-stranded oligonucleotide, wherein the oligonucleotide has a phosphodiester backbone, and wherein the oligonucleotide consists of SEQ ID NO: 11, SEQ ID NO:1, pTpT, SEQ ID NO:5 or a functional fragment of SEQ ID No:5.

44. A method of increasing DNA repair in skin of a mammal, comprising topically administering to the skin an effective amount of a composition consisting of pTpT or an oligonucleotide having a nucleotide sequence consisting of SEQ ID NO: 1.

45. A method of inhibiting growth of malignant skin cells of a mammal, said method comprising topically administering to said cells an effective amount of pTpT.

46. The method of claim 40, wherein the composition consisting of pTpT or a single-stranded DNA fragment having a nucleotide sequence consisting of SEQ ID NO: 1 with a 5' phosphate.

47. A method of inhibiting the growth of cells in a mammal, comprising directly administering to the cells of the mammal an effective amount of pTpT.

48. A method of inhibiting proliferation of epithelial cells, comprising directly administering to said cells an effective amount of a composition consisting of pTpT.

49. A method of inhibiting proliferation of skin cells in a mammal, comprising administering topically to the skin an effective amount of a composition comprising at least one oligonucleotide having a DNA sequence consisting of pTpT or SEQ ID NO:1.

50. A method of inhibiting proliferation of skin cells in a mammal, comprising administering topically to the skin of the mammal an effective amount of a composition consisting of pTpT.

51. The method of claim 50, wherein said skin cells are selected from the group consisting of: melanocytes, keratinocytes and fibroblasts.

52. A method of inhibiting growth of skin cells in a mammal, comprising administering to skin of the mammal an oligonucleotide having a nucleotide sequence consisting of pTpT, SEQ ID NO:1 or SEQ ID NO:6.

53. The method of claim 52 wherein the skin cells are keratinocytes.

54. A method of increasing melanin production in epidermal melanocytes of a mammal, said method comprising topically administering to said epidermal melanocytes an effective amount of a composition comprising at least one oligonucleotide, wherein the oligonucleotide has a phosphodiester backbone, and wherein the oligonucleotide has a nucleotide sequence consisting of SEQ ID NO: 1, SEQ ID NO: 2; SEQ ID NO:3 or SEQ ID NO:4.

55. A method of inhibiting growth of malignant skin cells in a mammal, said method comprising topically administering to the skin cells an effective amount of a composition comprising at least one oligonucleotide comprising a phosphodiester backbone, wherein the oligonucleotide consists of a sequence selected from the group consisting of SEQ ID NO: 1, SEQ ID NO: 6 and pTpT.

56. A method of treating hyperproliferative disease affecting epithelial cells in a mammal, comprising administering by aerosol to the epithelial cells an effective amount of a composition comprising at least one DNA oligonucleotide comprising a phosphodiester backbone, wherein the oligonucleotide has a nucleotide sequence consisting of SEQ ID NO: 1, SEQ ID NO:6 or pTpT.

57. A method of treating inhibiting growth of epithelial carcinoma cells in a mammal, comprising administering to the epithelial carcinoma cells an effective amount of a composition comprising at least one DNA oligonucleotide comprising a phosphodiester backbone, wherein the oligonucleotide has a nucleotide sequence consisting of SEQ ID NO: 1, SEQ ID NO:6 or pTpT.

* * * * *